Figure 1A:
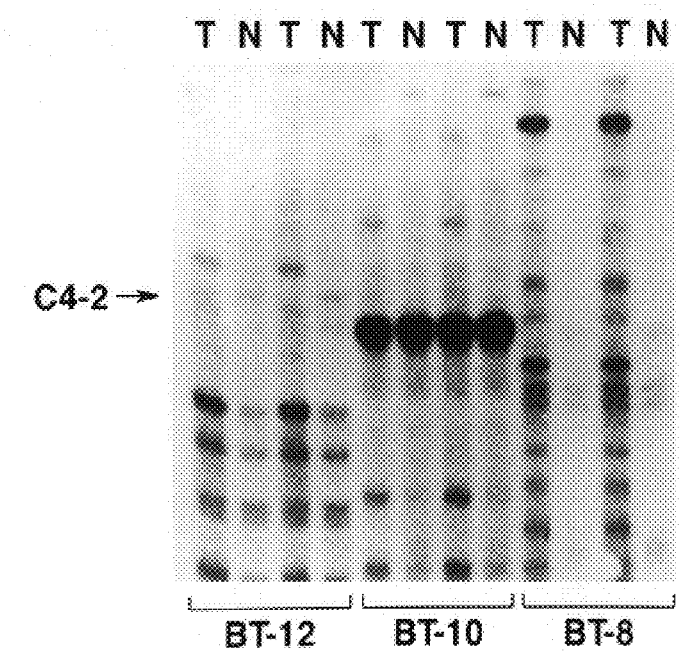

United States Patent [19]

Murphy et al.

[11] Patent Number: 5,990,294
[45] Date of Patent: Nov. 23, 1999

[54] NUCLEOTIDE AND AMINO ACID SEQUENCES OF C4-2, A TUMOR SUPPRESSOR GENE, AND METHODS OF USE THEREOF

[75] Inventors: Gerald P. Murphy, Seattle; Alton L. Boynton, Redmond; Anil Sehgal, Seattle, all of Wash.

[73] Assignee: Northwest Biotherapeutics LLC, Seattle, Wash.

[21] Appl. No.: 08/744,905

[22] Filed: Nov. 8, 1996

[51] Int. Cl.⁶ .................. C07H 21/04; G01N 33/574; C12N 15/00; C07K 1/00

[52] U.S. Cl. .................. 536/23.5; 435/7.23; 435/320.1; 530/350

[58] Field of Search .................. 536/23.5; 530/350, 530/358; 435/7.23, 320.1

[56] References Cited

PUBLICATIONS

Benton and Davis, 1977, "Screening λgt Recombinant Clones by Hybridization to Single Plaques in situ", Science 196:180–182.
Bogler et al., 1995, "The p53 Gene and Its Role in Human Brain Tumors", GLIA 15:308–327.
Boynton and Whitfield, 1983, "The Role of Cyclic AMP in Cell Proliferation: A Critical Assessment of the Evidence", Adv. Cyclo. Nucleo. Res. 15:193–294.
Brene et al., 1994, "Expression of m2RNAs Encoding ARPP–16/19, ARPP–21, and DARPP–32 in Human Brain Tissue", J. Neuroscience 14:985–998.
Chen et al., 1995, "Connexin43 Reverses the Phenotype of Transformed Cells and Alters Their Expression of Cyclin/Cyclin–Dependent Kinases", Cell Growth Differ. 6:681–690.
Faillot et al., 1996, "A Phase I Study of an Anti–Epidermal Growth Factor Receptor Monoclonal Antibody for the Treatment of Malignant Gliomas", Neurosurgery 39:478–483.
Furnari et al., 1995, "Genetics and Malignant Progression of Human Brain Tumours", Cancer Surveys 25:223–275.
Grunstein and Hogness, 1975, "Colony Hybridization: A Method for the Isolation of Cloned DNAs that Contain a Specific Gene", Proc. Natl. Acad. Sci. USA 72:3961–3965.
Hadman et al., 1995, "Modifications to the Differential Display Technique Reduce Background and Increase Sensitivity", Anal. Chem. 226:383–386.
Horiuchi et al., 1990, "Purification and cDNA Cloning of ARPP–16, a cAMP–Regulated Phosphoprotein Enriched in Basal Ganglia, and of Related Phosphoprotein, ARPP–19", J. Biol. Chem. 265:9476–9484.

Ikonomov and Jacob, 1996, "Differential Display Protocol with Selected Primers that Preferentially Isolates mRNAs of Moderate–to Low–Abundance in a Microscopic System", Biotechniques 20:1030–1042.
Laws and Thapar, 1993, "Brain Tumors", CA Cancer J. Clin. 43:262–271.
Liang et al., 1992, "Differential Display and Cloning of Messenger RNAs from Human Breast Cancer versus Mammary Epithelial Cells", Cancer Res. 52:6966–6968.
Liang and Pardee, 1992, "Differential Display of Eukaryotic Messenger RNA by Means of the Polymerase Chain Reaction", Science 257:967–971.
Parker et al., 1996, "Cancer Statistics, 1996", CA Cancer J. Clin. 46:5–28.
Ponder, 1990, Inherited Predisposition to Cancer, Trends Genet. 6:213–218.
Sehgal et al., 1996, "Isolation of Differentially Expressed cDNAs During Ferret Tracheal Development: Application of Differential Display PCR", Exp. Lung Res. 22:419–434.
Shilo and Weinberg, 1981, "DNA Sequences Homologous to Vertebrate Oncogenes Are Conserved in *Drosophila melanogaster*", Proc. Natl. Acad. Sci. USA 78:6789–6792.
Weinberg, 1991, "Tumor Supressor Genes", Science 254:1138–1146.
Harada et al., 1996, "Molecular Genetic Investigation of the Neurofibromatosis Type 2 Tumor Suppressor Gene in Sporadic Meningioma", J. Neurosurg. 84:847–851.
Sehgal et al., 1997, "Characterization of C4–2 as a Tumor–Suppressor Gene in Human Brain Tumors", J. Surg. Oncol. 64:102–108.
Sehgal et al., 1997, "Cloning, Sequence and Developmental Expression Analysis of C4–2, a Potential Brain Tumor–Suppressor Gene", J. Surg. Oncol. 65:249–257.

*Primary Examiner*—Sheela Huff
*Assistant Examiner*—Yvonne Eyler
*Attorney, Agent, or Firm*—Pennie & Edmonds LLP

[57] ABSTRACT

The present invention relates to the discovery, identification and characterization of a novel tumor suppressor gene C4-2. The invention encompasses nucleotide sequences of the C4-2 gene and amino acid sequences of its encoded protein product(s), as well as derivatives and analogs thereof. The invention also encompasses the production of C4-2 proteins and antibodies. The invention further encompasses therapeutic compositions and methods of diagnosis and therapy.

5 Claims, 7 Drawing Sheets

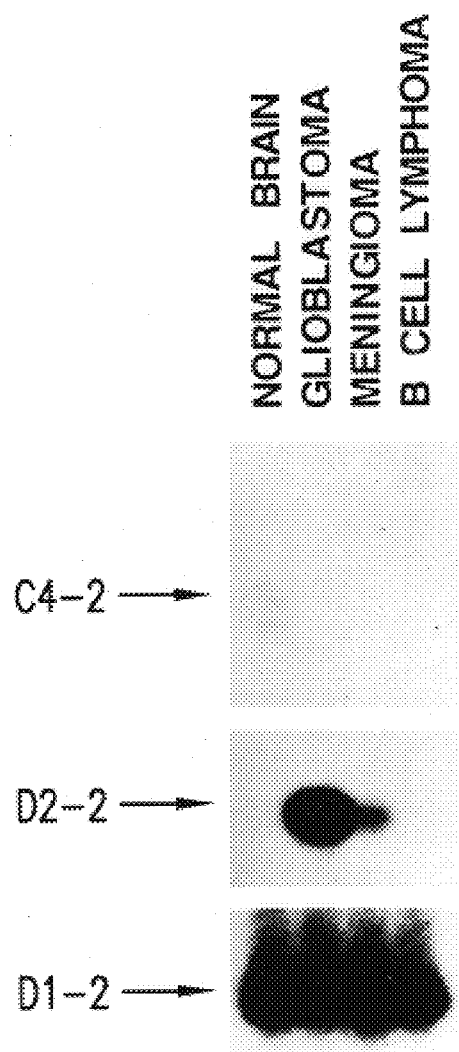
FIG.2A
FIG.2B
FIG.2C
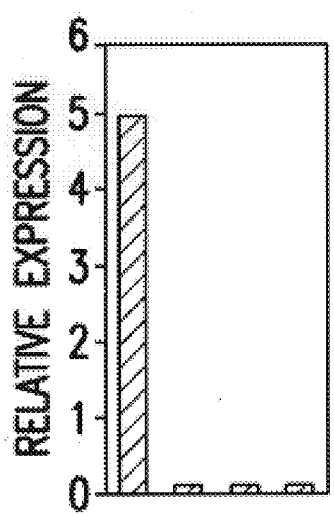
FIG.2D

| ARPP-16 | TAGCAGTACC | CATGACATTC | AGTGGCCTTG | TGCAAATATG | GTATGTTGC- |
| C4-2 | GTACTG-ATC | CATGACATTC | AGTGGCCTTG | TGCAAATACG | ATATGTTGCC |

| ARPP-16 | TTAGGCATAT | GTTTTGTGCT | AGGAGAACG | TTTCATTTTG | ACTTTTAT-G |
| C4-2 | TTAGGCATAT | CTTTTGTGCT | ATGCCAGAAC | CTTTATTTTG | ATTTTTTTCG |

| ARPP16 | AAAATTACTG | TTCATATAGT | TTATATAAAC | TTTTTTAATG | -TAGAAAGT |
| C4-2 | AAAGTTGCAA | TTGATGTAAT | TTATATAAAC | TTTTTAAATA | GCTAGAAAGT |

| ARPP-16 | TTTTTACTTGC | ACAGTCAATT | TAGGGACAC | -TAGAATAAA | AGACTTTGCC |
| C4-2 | TTTTTACTTCC | ACACTCAGTT | TTGGAGACC | CTAGAATAAA | AGGCTTCAAT |

| ARPP-16 | TCTTGTGGCC | CCTCCCTTCT | TTTTTTTTGC | TTCTT | |
| C4-2 | ACTC-TG--- | CATTCCCGAA | AAAAAAAAAA | AAAAA | |

FIG. 3

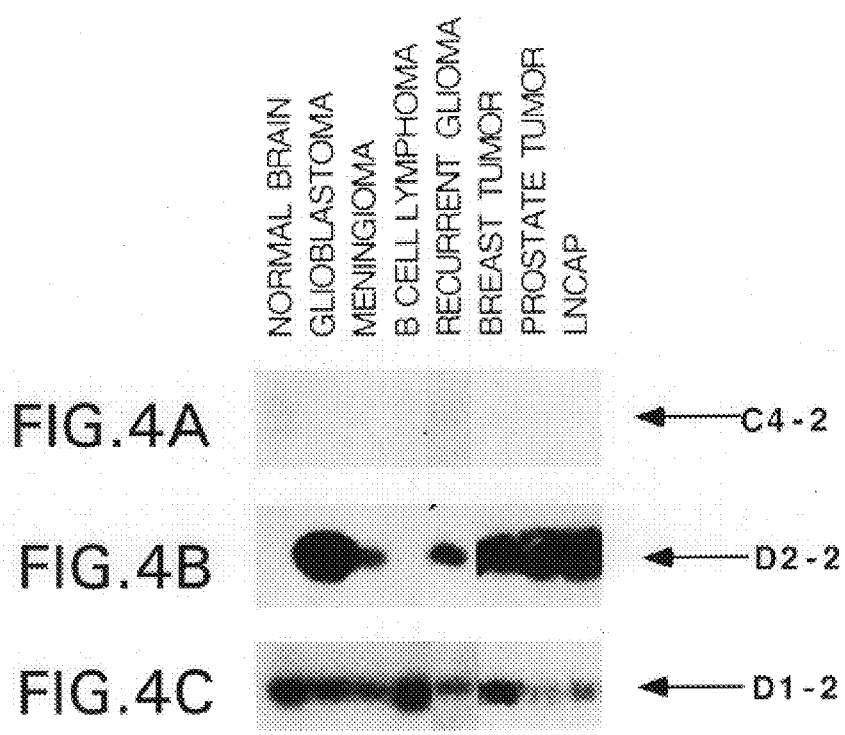
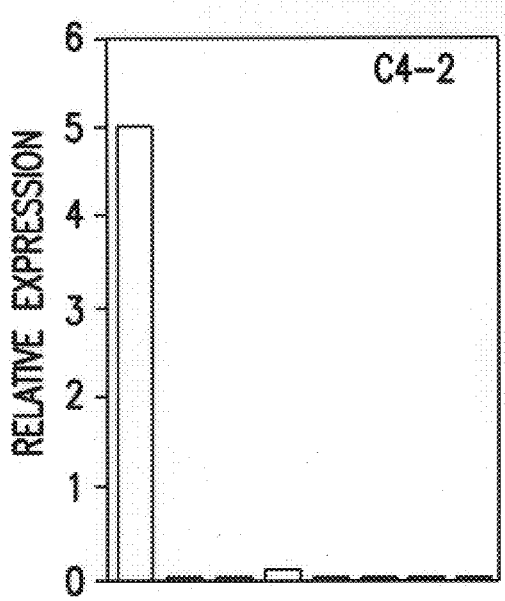
FIG.4D
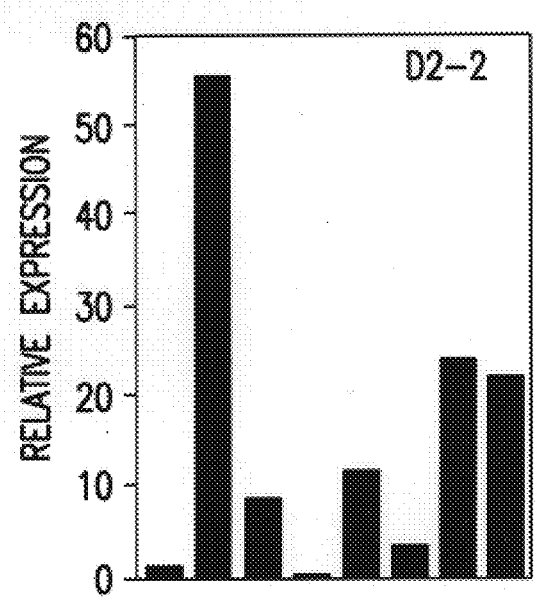
FIG.4E

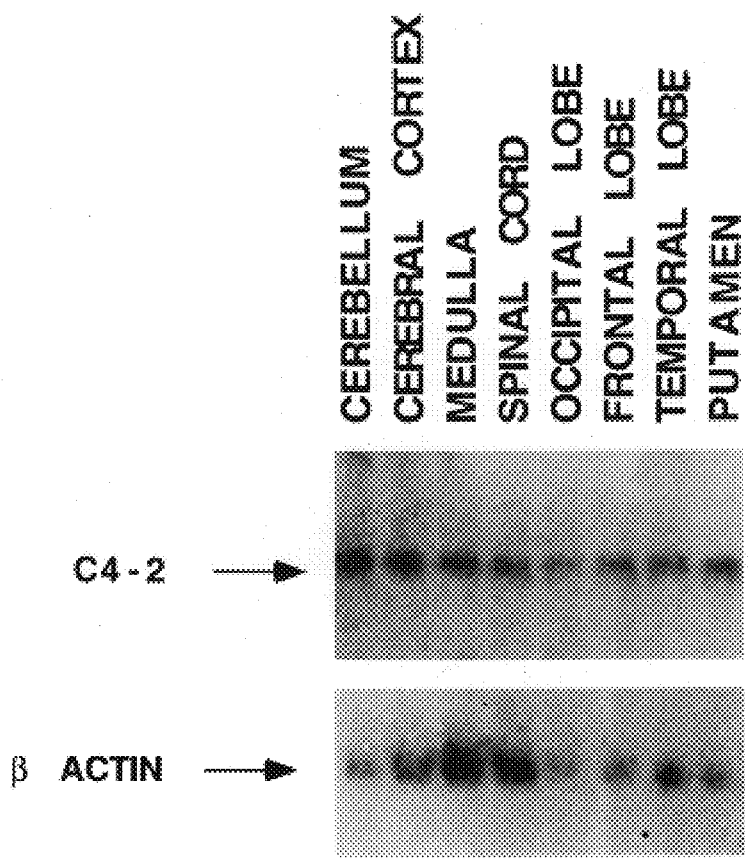
FIG.6A
FIG.6B
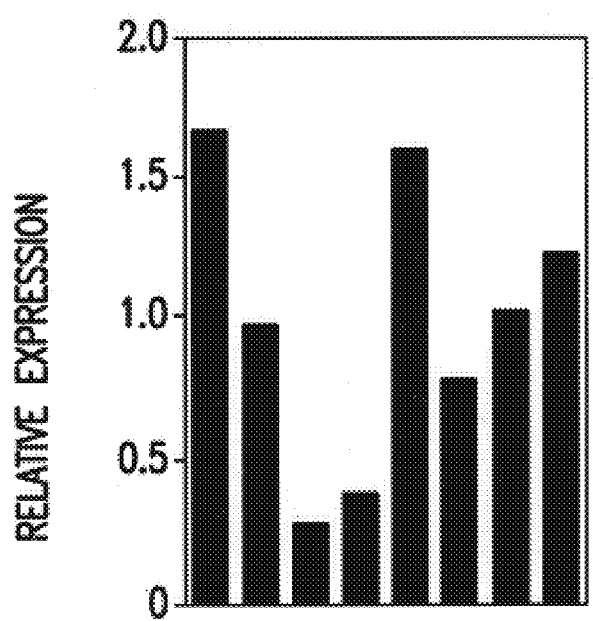
FIG.6C

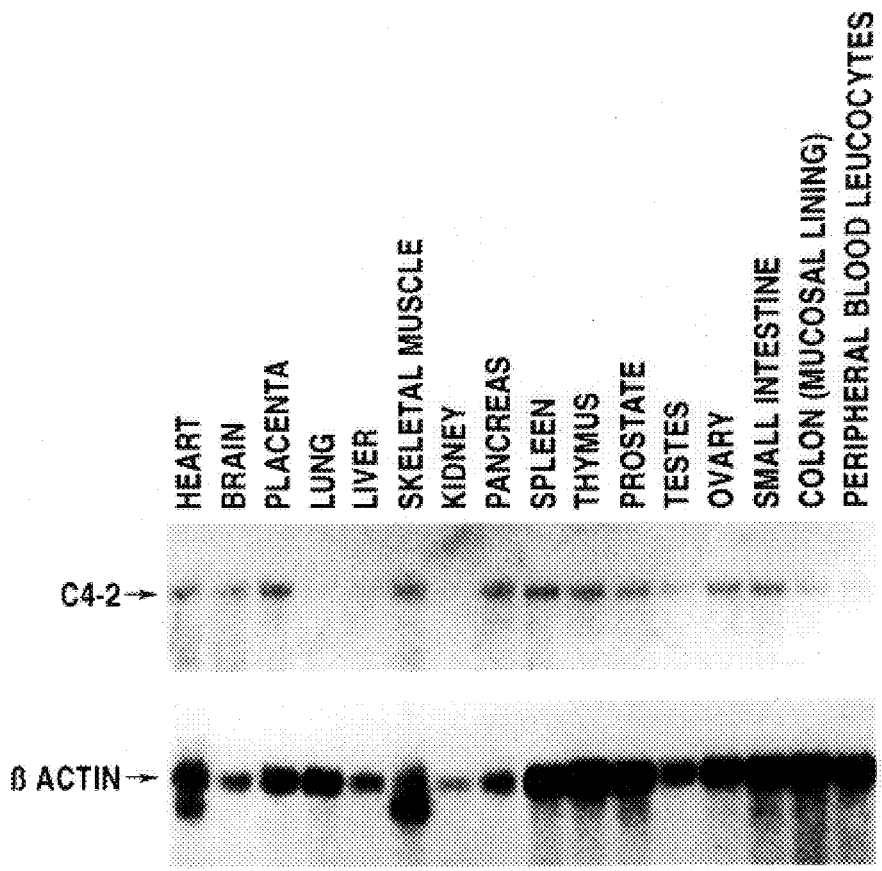
FIG. 7A
FIG. 7B
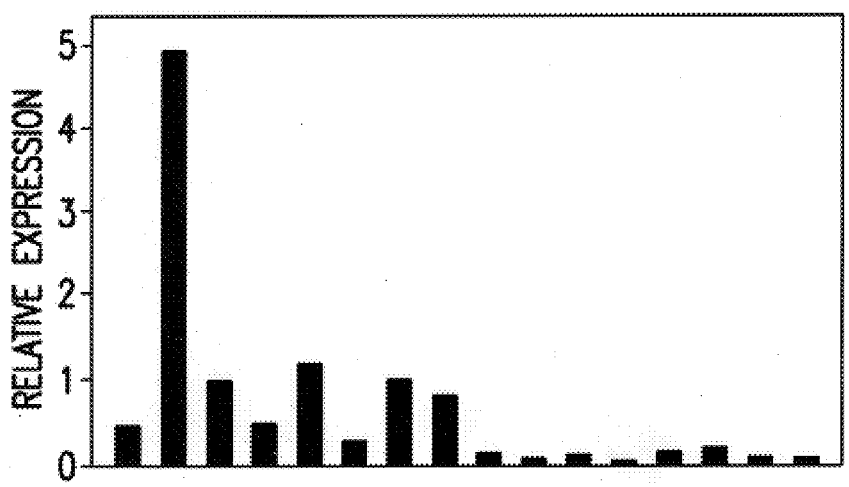
FIG. 7C

SEQUENCE LISTING

```
(1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 236 base pairs
        (B) TYPE: nucleic acid
        (C) STRANDEDNESS: single
        (D) TOPOLOGY: linear (ix) FEATURE:
        (A) NAME/KEY: Modified Base
        (B) LOCATION: 50
        (D) OTHER INFORMATION: Where N is any nucleotide
        (A) NAME/KEY: Modified Base
        (B) LOCATION: 99
        (D) OTHER INFORMATION: Where N is any nucleotide
        (A) NAME/KEY: Modified Base
        (B) LOCATION: 141...142
        (D) OTHER INFORMATION: Where N is any nucleotide
        (A) NAME/KEY: Modified Base
        (B) LOCATION: 181
        (C) OTHER INFORMATION: Where N is any nucleotide
```

(xi) SEQUENCE DESCRIPTION: SEQ ID NO:1:

TAGCAGTACC CATGACATTC AGTGGCCTTG TGCAAATATG GTATGGTTGC NTTAGGCATA        60

TCTTTTGTCC TAGGCAGAAC GTTTCATTTT GACTTTTATN GAAAATTACT GTTCATATAG       120

TTTATATAAA CTTTTTTAAT GNNTAGAAAC TTTTTACTTG CACAGTCAAT TTAGGGGACA       180

CNTAGAATAA AAGACTTTGC CTCTTGTGGC CCCTCCCTTC TTTTTTTTTG CTTCTT          236

(2) INFORMATION FOR SEQ ID NO:2:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (ix) FEATURE:
        (A) NAME/KEY: Modified Base
        (B) LOCATION: 7
        (D) OTHER INFORMATION: Where N is any nucleotide
        (A) NAME/KEY: Modified Base
        (B) LOCATION: 205
        (D) OTHER INFORMATION: Where N is any nucleotide
        (A) NAME/KEY: Modified Base
        (B) LOCATION: 208...210
        (D) OTHER INFORMATION: Where N is any nucleotide (xi) SEQUENCE DESCRIPTION: SEQ ID NO:2:

GTACTGNATC CATGACATTC AGTGGCCTTG TGCAAATACG ATATGTTGCC TTAGGCATAT        60

CTTTTGTCCT ATGCCAGAAC CTTTATTTTG ATTTTTTTCG AAAGTTGCAA TTCATGTAAT       120

TTATATAAAC TTTTTAAATA GCTAGAAACT TTTTACTTCC ACACTCAGTT TTGGAGACCC       180

CTAGAATAAA AGGCTTTGCC ACTCNTGNNN CATTCCCGAA AAAAAAAAA AAAAA            235

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE:
        (A) NAME/KEY: Modified Base
        (B) LOCATION: 1
        (D) OTHER INFORMATION: Where N is any nucleotide (xi) SEQUENCE DESCRIPTION: SEQ ID NO:3:

NTACTGATCC ATGACA                                                       16

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ix) FEATURE:
        (A) NAME/KEY: Modified Base
        (B) LOCATION: 1
        (D) OTHER INFORMATION: Where N is any nucleotide (xi) SEQUENCE DESCRIPTION: SEQ ID NO:4:

NGTGCTCTCA TACT                                                         14

(2) INFORMATION FOR SEQ ID NO:5:

(i) SEQUENCE CHARACTERISTICS:

```
            (A) LENGTH: 17 base pairs
            (B) TYPE: nucleic acid
            (C) STRANDEDNESS: single
            (D) TOPOLOGY: linear (ix) FEATURE:
            (A) NAME/KEY: Modified Base
            (B) LOCATION: 1
            (D) OTHER INFORMATION: Where N is any nucleotide (xi) SEQUENCE DESCRIPTION: SEQ ID NO:5:

NTGATCTAAG GCACATA                                                17

(2) INFORMATION FOR SEQ ID NO:6:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:6:

TGATCCATGA CATTCAGTG                                              19

(2) INFORMATION FOR SEQ ID NO:7:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:7:

GGAATGCAGA GTATTGAAG                                              19

(2) INFORMATION FOR SEQ ID NO:8:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:8:

CTCAGTGTTA ACGGATAAT                                              19

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:9:

TGTTGAGAAG AGTACATCTT                                             20

(2) INFORMATION FOR SEQ ID NO:10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:10:

CGGAGCAATA TGAAATGATC T                                           21
```

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:11:

GCAAATACAG CTCCTATTG                                            19

(2) INFORMATION FOR SEQ ID NO:12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:12:

TTGTGCAAAT ACGATATGTT GCCTTAGGCA TATCTTTTGT                40

(2) INFORMATION FOR SEQ ID NO:13:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:13:

CCAAACTGGA CATCAAGGAA TTGCTACACA GAAGAACCAC CATCCAGGAT AGAA      54

(2) INFORMATION FOR SEQ ID NO:14:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:14:

TAGGCCTGAC TGGCATTGTA TTAGCAAACT CATCACTAGA                40

NUCLEOTIDE AND AMINO ACID SEQUENCES OF C4-2, A TUMOR SUPPRESSOR GENE, AND METHODS OF USE THEREOF

1. FIELD OF THE INVENTION

The present invention relates to the discovery, identification and characterization of a novel tumor suppressor gene C+b 4-+b 2. The invention encompasses nucleotide sequences of the C+b 4-+b 2 gene and amino acid sequences of its encoded protein product(s), as well as derivatives and analogs thereof. The invention also encompasses the production of C4-2 proteins and antibodies. The invention further encompasses therapeutic compositions and methods of diagnosis and therapy.

2. BACKGROUND

Brain tumors have claimed the lives of 13,300 people in 1995. The number of deaths caused by brain tumors are increasing each year. Over 17,900 will die in 1996. Brain tumors claim lives of not only adults but also of children. The increased incidence of brain tumors is not only evident in the young but also in adults. It has been documented that a significant increase in mortality has occurred in adult primary malignant brain tumors between 1982 and 1996 (Parker et al., 1996, CA Cancer J. Clin. 46:5–28).

Glioblastomas, astrocytomas and meningiomas are the most common brain tumors that affect adults. Glioblastoma multiforme are high grade astrocytomas that grow very rapidly and contain cells that are malignant (Laws and Thapar, 1993, CA Cancer J. Clin. 43:262–271). The molecular basis of glioblastoma multiforme may involve systematic events at the chromosomal level or at the gene expression level. These may include inactivation of tumor suppressor genes, activation of oncogenes or specific translocations at the chromosomal level. Genetic changes at the chromosomal level and gene expression level are well documented for other brain tumors (Furnari et al., 1995. Cancer Surveys 25:223–275).

Tumor suppressor genes play an important role in normal cell growth, differentiation and progression through the cell cycle. Tumor suppressor genes in humans have been identified through studies of genetic changes occurring in cancer cells (Ponder, 1990, Trends Genet. 6:213–218; Weinberg, 1991, Science 254:1138–1146). Mutations that cause change in gene expression of tumor suppressor genes lead to cell transformation in vitro and tumor development in vivo. It has been documented that loss of tumor suppressor(s) genes at chromosome 10, mutations in p53 or overexpression of epidermal growth factor receptor may be major events leading to glioblastoma multiforme (Furnari et al., 1995, Cancer Surveys 25:223–271; Bogler et al., 1995, GLIA 15:308–327; Faillot et al., 1996, Neurosurgery 39:478–483). The exact series of events involving tumor suppressor genes that lead to initiation and progression of glioblastoma is not known.

Citation of references in this section or any section of this application shall not be construed as an admission that such references are available as prior art to the present invention.

3. SUMMARY OF THE INVENTION

The present invention relates to the discovery, identification and characterization of a novel tumor suppressor gene, C+b 4-+b 2. C+b 4-+b 2, described for the first time herein, was found to be expressed at high levels in normal brain tissue and at very low levels in several brain tumors.

The present invention encompasses nucleotide sequences of the C+b 4-+b 2 gene, and amino acid sequences of its encoded protein, as well as derivatives (e.g., fragments) and analogs thereof. The nucleotide sequences of the present invention encompass nucleotide sequences of the human C+b 4-+b 2 gene and C+b 4-+b 2 homologs of other species. The present invention also relates to nucleic acids hybridizable to or complementary to the foregoing nucleotide sequences. In a specific embodiment, C4-2 is a human gene and the C+b 4-+b 2 protein is a human protein.

The present invention also encompasses fragments of C4-2, and derivatives and analogs thereof, which comprise one or more domains of a C4-2 protein. The invention further encompasses antibodies to C4-2 and C4-2 derivatives and analogs. The invention still further encompasses methods of production of the C4-2 protein fragments, derivatives and analogs.

The present invention also encompasses therapeutic and diagnostic methods and compositions based on C4-2 proteins and nucleic acids. Therapeutic compounds of the invention include but are not limited to C4-2 proteins and analogs and derivatives (including fragments) thereof; antibodies thereto; nucleic acids encoding the C4-2 proteins, analogs, or derivatives; and C+b 4-+b 2 antisense nucleic acids.

The invention encompasses methods of treatment of disorders of overproliferation (e.g., cancer and hyperproliferative disorders) by administering compounds that enhance or promote C4-2 activity (e.g., C4-2, an agonist of C4-2; nucleic acids that encode C4-2).

The invention also provides methods of treatment of disorders involving deficient cell proliferation (growth) or in which cell proliferation is otherwise desired (e.g., degenerative disorders, growth deficiencies, lesions, physical trauma) by administering compounds that decrease or antagonize (inhibit) C4-2 function (e.g., antibodies, antisense nucleic acids, ribozymes and triple helix molecules).

The invention also encompasses animal models, diagnostic methods and screening methods for predisposition to disorders, and methods to identify C4-2 agonists and antagonists.

3.1. DEFINITIONS

As used herein, the following terms or abbreviations, whether used in the singular or plural, will have the meanings indicated:

C+b 4-+b 2 nucleotides or coding sequences: means nucleotide sequences encoding C4-2 protein, polypeptide or peptide fragments of C4-2 protein, or C4-2 fusion proteins. C+b 4-+b 2 nucleotide sequences encompass DNA, including genomic DNA (e.g. the C+b 4-+b 2 gene) and cDNA, and RNA.

C4-2: means the C4-2 protein. Polypeptides or peptide fragments of C4-2 protein are referred to as C4-2 polypeptides or C4-2 peptides. Fusions of C4-2, or C4-2 polypeptides or peptide fragments to an unrelated protein are referred to herein as C4-2 fusion proteins. A functional C4-2 protein or peptide refers to a protein which displays one or more known functional activities associated with a full-length (wild-type) C4-2 protein, e.g., inhibition of cell proliferation, binding to a C4-2 substrate or C4-2 binding partner, antigenicity (binding to an anti-C4-2 antibody), immunogenicity, etc., with high affinity in vivo or in vitro.

ECD: means "extracellular domain".
TM: means "transmembrane domain".
CD: means "cytoplasmic domain".

4. DESCRIPTION OF THE FIGURES

Figure 1B:
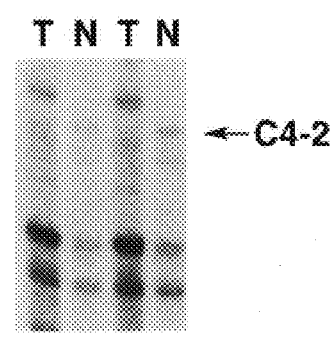

The present invention may be understood more fully by reference to the following detailed description of the invention, examples of specific embodiments of the invention and the appended figures in which:

FIG. 1A–B. Identification of differentially expressed genes from glioblastoma multiforme tumor tissue and normal brain tissue using differential display PCR. FIG. 1A is an autoragiogram of DD-PCR using three 5' specific primers: 5' primers (BT-8 5'NTACTGATCCATGACA3' SEQ ID NO:3, BT-10, 5'NGTGCTCTCATACT3' SEQ ID NO:4 and BT-12 5'NTGATCTAAGGCACATA3' SEQ ID NO:5) and the protocol previously published (Hadman et al., 1995, Anal Chem. 226:383–386). FIG. 1B shows the expression of C4-2 in detail. Note the expression of the C4-2 gene (arrow) in normal tissue (N) and not in tumor tissue (T).

FIG. 2A–D. C4-2 is expressed in normal brain but not in glioblastoma or meningioma primary brain tumor tissue or B cell lymphoma. FIG. 2A is an autoradiogram of a RT-PCR for C4-2. FIG. 2A is an autoradiogram of a RT-PCR for D2-2, which is a gene overexpressed in glioblastoma. FIG. 2C is an autoradiogram for D1-2; a housekeeping gene equally expressed in a wide variety of tissues and is used as an internal control for gel loading. FIG. 2D is a bar graph which represents the relative expression of C4-2 in these tissues after correction for gel loading based on D1-2 expression. See text Section 6.1.3 for experimental details.

FIG. 3. Partial nucleotide sequence of C4-2 showing sequence homology of C4-2 with ARPP-16. Sequence of C4-2 was matched with ARPP-16 using the BLAST DNA program. Shaded boxes represent areas of strong homology. A small portion of C4-2 has 66.8% nucleotide sequence identity to a portion of the nucleotide sequence ARPP-16 which encodes a cyclic AMP regulated phosphoprotein.

FIGS. 4A–4E. C4-2 in not expressed or minimally expressed in tumor tissues. Total RNA was isolated from several normal and tumor tissues. RT-PCR for C4-2, D2-2 and D1-2 was performed as described in text Section 6.1.3. FIG. 4A–C shows suppression of C4-2 expression in tumor tissues, FIG. 4B shows D2-2 expression in tumor tissues, and the FIG. 4C shows D1-2 expression in tumors as an internal control. FIG. 4D and 4E is a bar graph which shows the relative expression of C4-2 and D2-2 in tumor tissues after correction for gel loading based on D1-2 expression. C4-2 is not expressed or is minimally expressed in a wide variety of tumor tissues.

Figures 5A, 5B, 5C, 5D:
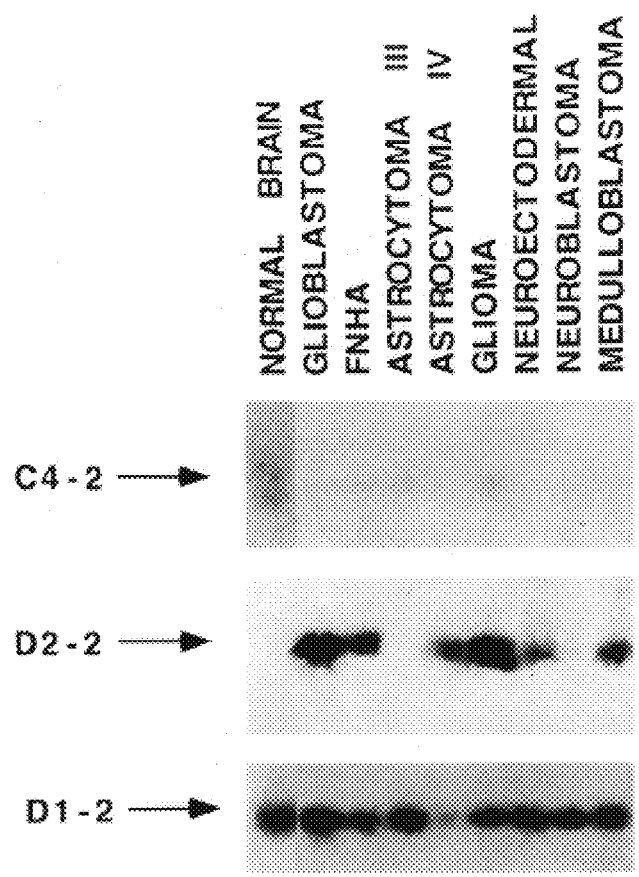

FIGS. 5A–5D. Expression of C4-2 in brain tumor cell lines and Normal Human Astrocytes (NHA). Human brain tumor cell lines (Glioblastoma, AstrocytomaIII, AstrocytomaIV, Glioma, Medulloblastoma, Neuroectodermal, Neuroblastoma) were grown to 80% confluency in appropriate media suggested by the vendor. PCR and Southern blot analysis were performed. FIG. 5A is an autoradiogram of a Southern blot of C4-2 expression, FIG. 5B is an autoradiogram of a Southern blot of D2-2 expression, FIG. 5C is an autoradiogram of a Southern blot of D1-2 expression in various brain tumor cell lines and in normal fetal human astrocytes. FIG. 5D is a bar graph which represents the relative expression of C4-2 and D2-2 in respective cell lines after correction gel loading based on D1-2 expression. C4-2 is not expressed in most brain tumor cell lines nor in fetal brain astrocytes compared to normal tissue.

FIGS. 6A–6C. Expression of C4-2 in different regions of the normal adult brain. FIG. 6A is a autoradiogram of a Northern blot of C4-2 expression in different regions of normal adult brain, and FIG. 6B is an autoradiogram of a northern blot of β actin expression, which serves as an internal control for gel loading. FIG. 6C is a bar graph which shows the relative expression of C4-2 in different regions of the brain as quantitated using Imagequant (Molecular Dynamics). C4-2 is widely expressed in different regions of tissue of normal human brain.

FIGS. 7A–7C. Expression of C4-2 in normal human tissues. FIG. 7A is an autoradiogram of a Northern blot of C4-2 expression in various normal human tissues. FIG. 7B is an autoradiogram of a Northern blot of β actin expression in various normal human tissues, which serves as an internal control for gel loading. FIG. 7C is a bar graph which shows the relative expression of C4-2 in various normal human tissues. C4-2 expression in normal tissues is highest in the brain.

5. DETAILED DESCRIPTION OF THE INVENTION

The present invention relates to the discovery, identification and characterization of a novel tumor suppressor gene, C4-2. C4-2, described for the first time herein, was found to be expressed at high levels in normal brain tissue and at very low levels in glioblastoma multiforme tissue and in several brain tumors.

The present invention encompasses nucleotide sequences of the C4-2 gene, and amino acid sequences of its encoded protein. The invention further encompasses fragments and other derivatives, and analogs, of C4-2 proteins. Nucleic acids encoding such fragments or derivatives are also within the scope of the invention. The invention encompasses C4-2 genes and their encoded proteins of many different species. The C4-2 genes of the invention include human and other mammalian and related genes (homologs) in other species. In a preferred embodiment the C4-2 gene is human.

The invention encompasses the following nucleotides, host cells expressing such nucleotides, and the expression products of such nucleotides: (a) nucleotides that encode mammalian C4-2, including the human C4-2, and the C4-2 gene product; (b) nucleotides that encode portions of C4-2 that correspond to its functional domains, and the polypeptide products specified by such nucleotide sequences; (c) nucleotides that encode mutants of the C4-2 in which all or a part of one of the domains is deleted or altered, and the polypeptide products specified by such nucleotide sequences; (d) nucleotides that encode fusion proteins containing C4-2 or one of its domains fused to another polypeptide.

The invention also encompasses agonists and antagonists of C4-2, including small molecules, large molecules, mutant C4-2 proteins that compete with native C4-2, and antibodies, as well as nucleotide sequences that can be used to inhibit C4-2 gene expression (e.g., antisense and ribozyme molecules, and gene or regulatory sequence replacement constructs) or to enhance C4-2 gene expression (e.g., expression constructs that place the C4-2 gene under the control of a strong promoter system), and transgenic animals that express a C4-2 transgene or "knockouts" that do not express C4-2.

In addition, the present invention encompasses methods and compositions for the diagnostic evaluation, typing and prognosis of cancers and tumors, in particular, brain tumors, and for the identification of subjects having a predisposition to such conditions. For example, C+b 4-+b 2 nucleic acid molecules of the invention can be used as diagnostic hybridization probes or as primers for diagnostic PCR analysis for the identification of C+b 4-+b 2 gene mutations, allelic variations and regulatory defects in the C+b 4-+b 2 gene. The present invention further provides for diagnostic kits for the practice of such methods.

Further, the present invention also relates to methods for the use of the C+b 4-+b 2 gene and/or C+b 4-+b 2 gene products for the identification of compounds which modulate, i.e., act as agonists or antagonists, of C+b 4-+b 2 gene expression and or C+b 4-+b 2 gene product activity. Such compounds can be used as agents for treatment of disorders of cellular overproliferation and, in particular, as therapeutic agents for the treatment of brain tumors.

Still further, the invention encompasses methods and compositions for the treatment of disorders of cellular overproliferation and cancers and tumors, in particular brain tumors. Such methods and compositions are capable of modulating the level of C+b 4-+b 2 gene expression and/or the level of C+b 4-+b 2 gene product activity.

This invention is based, in part, on the surprising discovery of the tumor suppressor gene C+b 4-+b 2. C+b 4-+b 2 was identified using the technique of Differential Display-PCR to identify genes that are overexpressed in normal brain tissue as compared to glioblastoma multiforme tissue. C+b 4-+b 2 was found to be expressed in normal human brain tissue at high levels and at low levels in the majority of other types of tissues, including heart, lung, muscle. C+b 4-+b 2 was also found to be expressed at very low levels in glioblastoma brain tumors, meningiomas, in addition to other tumor tissues. The nucleotide sequence of a small portion of C+b 4-+b 2 was also found to have 66.8% homology to a portion of a nucleotide sequence which encodes a previously isolated protein, ARPP-16 a cAMP-regulated phosphoprotein. ARPP-16 is a potential mediator of hormones and neurotransmitters that raises cAMP levels in cells, a critical cell cycle mediator (Boynton and Whitfield, 1983, Adv. Cyclic Nucleo. Res. 15:193–294).

Various aspects of the invention are described in greater detail in the subsections below.

5.1. THE C4-2 GENE

The invention relates to the nucleotide sequences of C+b 4-+b 2 nucleic acids. In specific embodiments, C+b 4-+b 2 nucleic acids comprise the cDNA sequence of FIG. 3 (SEQ ID NO:2), or the coding regions of C+b 4-+b 2, or nucleotide sequences encoding a C4-2 protein. The invention provides purified nucleic acids consisting of at least 6 contiguous nucleotides (i.e., a hybridizable portion) of a C+b 4-+b 2 sequence; in other embodiments, the nucleic acids consist of at least 8 (continuous) nucleotides, 25 nucleotides, 50 nucleotides, 100 nucleotides, 150 nucleotides, 200 nucleotides, or 250 nucleotides of a C+b 4-+b 2 sequence. In another embodiment, the nucleic acids are smaller than 35, 200 or 250 nucleotides in length. Nucleic acids can be single or double stranded. The invention also relates to nucleic acids hybridizable to or complementary to the foregoing sequences. In specific aspects, nucleic acids are provided which comprise a sequence complementary to at least 10, 25, 50, 100, 200, or 250 nucleotides of a C+b 4-+b 2 gene. In a specific embodiment, a nucleic acid which is hybridizable to a C+b 4-+b 2 nucleic acid (e.g., having sequence SEQ ID NO:2), or to a nucleic acid encoding a C4-2 derivative, under conditions of low stringency is provided.

By way of example and not limitation, procedures using such conditions of low stringency are as follows (see also Shilo and Weinberg, 1981, Proc. Natl. Acad. Sci. U.S.A. 78:6789–6792): Filters containing DNA are pretreated for 6 h at 40° C. in a solution containing 35% formamide, 5× SSC, 50 mM Tris-HCl (pH 7.5), 5 mM EDTA, 0.1% PVP, 0.1% Ficoll, 1% BSA, and 500 $\mu$g/ml denatured salmon sperm DNA. Hybridizations are carried out in the same solution with the following modifications: 0.02% PVP, 0.02% Ficoll, 0.2% BSA, 100 $\mu$g/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2× SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

In another specific embodiment, a nucleic acid which is hybridizable to a C+b 4-+b 2 nucleic acid under conditions of high stringency is provided. By way of example and not limitation, procedures using such conditions of high stringency are as follows: Prehybridization of filters containing DNA is carried out for 8 h to overnight at 65° C. in buffer composed of 6× SSC, 50 mM Tris-HCl (pH 7.5), 1 mM EDTA, 0.02% PVP, 0.02% Ficoll, 0.02% BSA, and 500 $\mu$g/ml denatured salmon sperm DNA. Filters are hybridized for 48 h at 65° C. in prehybridization mixture containing 100 $\mu$g/ml denatured salmon sperm DNA and 5–20×10$^6$ cpm of $^{32}$P-labeled probe. Washing of filters is done at 37° C. for 1 h in a solution containing 2× SSC, 0.01% PVP, 0.01% Ficoll, and 0.01% BSA. This is followed by a wash in 0.1× SSC at 50° C. for 45 min before autoradiography. Other conditions of high stringency which may be used are well known in the art.

In another specific embodiment, a nucleic acid, which is hybridizable to a C+b 4-+b 2 nucleic acid under conditions of moderate stringency is provided. By way of example and not limitation, procedures using such conditions of moderate stringency are as follows: Prehybridization of filters containing DNA is carried out for 8 h to overnight at 55° C. in buffer composed of 6×SSC, 50 mM Tris-HCl (pH 7.5), 1 mM EDTA, 0.02% PVP, 0.2% Ficoll, 0.02% BSA and 500 $\mu$g/ml denatured Salmon sperm DNA. Filters are hybridized for 24 h at 55° C. in prehybridization mixture containing 100 $\mu$g/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA.

Various other stringency conditions which promote DNA hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2× SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M NaHPO$_4$ (pH 7.2)/1 mM EDTA/7% SDS, or hybridization in 50% formamide/0.25M NaHPO$_4$ (pH 7.2)/0.25M NaCl/1 mM EDTA/7% SDS; followed by washing in 40 mM NaHPO$_4$ (pH 7.2)/1 mM EDTA/5% SDS at 50° C. or in 40 mM NaHPO$_4$ (pH 7.2) 1 mM EDTA/1% SDS at 50° C. Both temperature and salt may be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., 1989, Molecular Cloning, A Laboratory Manual, Second Edition, Cold Spring Harbor Press, N.Y., pp. 9.47–9.57; and Ausubel et al., 1989, Current Protocols in Molecular Biology, Green Publishing Associates and Wiley Interscience, N.Y.

Nucleic acids encoding derivatives and analogs of C4-2 proteins (see Sections 5.6 and 5.6.1), and C+b 4-+b 2 antisense nucleic acids (see Section 5.8.2.2.1) are additionally provided. As is readily apparent, as used herein, a "nucleic acid encoding a fragment or portion of a C4-2 protein" shall be construed as referring to a nucleic acid encoding only the recited fragment or portion of the C4-2 protein and not the other contiguous portions of the C4-2 protein as a continuous sequence.

Fragments of C+b 4-+b 2 nucleic acids comprising regions conserved between other C+b 4-+b 2 nucleic acids, of the same or different species, are also provided. Nucleic acids encoding one or more C4-2 domains are provided.

Specific embodiments for the cloning of a C+b 4-+b 2 gene, presented as a particular example but not by way of limitation, follow.

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed C4-2 product. In one embodiment, anti-C4-2 antibodies can be used for selection.

In another embodiment, polymerase chain reaction (PCR) is used to amplify the desired sequence in a genomic or cDNA library, prior to selection. Oligonucleotide primers representing known C+b 4-+b 2 sequences can be used as primers in PCR. In a preferred aspect, the oligonucleotide primers represent at least part of the C+b 4-+b 2 conserved segments of strong homology between C+b 4-+b 2 of different species. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known C+b 4-+b 2 nucleotide sequence and the nucleic acid homolog being isolated. For cross species hybridization, low stringency conditions are preferred. For same species hybridization, moderately stringent conditions are preferred. After successful amplification of a segment of a C+b 4-+b 2 homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding C4-2 proteins and C4-2 analogs may be identified The above-methods are not meant to limit the following general description of methods by which clones of C+b 4-+b 2 may be obtained.

Any eukaryotic cell potentially can serve as the nucleic acid source for the molecular cloning of the C+b 4-+b 2 gene. The nucleic acid sequences encoding C4-2 can be isolated from vertebrate sources including, mammalian sources such as, porcine, bovine, feline, avian, equine, canine, human as well as additional primate sources, avian, reptilian, amphibian, piscine, etc., from non-vertebrate sources, such as insects, from plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a C+b 4-+b 2 (of any species) gene or its specific RNA, or a fragment thereof (see Section 5.6), is available and can be purified and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, promotion of cell proliferation activity, substrate binding activity, or antigenic properties as known for C4-2. If an antibody to C4-2 is available, the C4-2 protein may be identified by binding of labeled antibody to the putatively C4-2 synthesizing clones, in an ELISA (enzyme-linked immunosorbent assay)-type procedure.

The C+b 4-+b 2 gene can also be identified by mRNA selection by nucleic acid hybridization followed by in vitro translation. In this procedure, fragments are used to isolate complementary mRNAs by hybridization. Such DNA fragments may represent available, purified C+b 4-+b 2 DNA of another species (e.g., human, mouse, etc.). Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against C4-2 protein. A radiolabelled C+b 4-+b 2 cDNA can be synthesized using the selected mRNA (from the adsorbed polysomes) as a template. The radiolabelled mRNA or cDNA may then be used as a probe to identify the C+b 4-+b 2 DNA fragments from among other genomic DNA fragments.

Alternatives to isolating the C+b 4-+b 2 genomic DNA include, but are not limited to, chemically synthesizing the gene sequence itself from a known sequence or making cDNA to the mRNA which encodes the C4-2 protein. For example, RNA for cDNA cloning of the C+b 4-+b 2 gene can be isolated from cells which express C+b 4-+b 2. Other methods are possible and within the scope of the invention.

The identified and isolated gene can then be inserted into an appropriate cloning vector A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and C+b 4-+b 2 gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated C+b 4-+b 2 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The C+b 4-+b 2 sequences provided by the present invention include those nucleotide sequences encoding substantially the same amino acid sequences as found in native C4-2 proteins, and those encoded amino acid sequences with functionally equivalent amino acids, as well as those encoding other C4-2 derivatives or analogs, as described in Sections 5.6 and 5.6.1 infra for C4-2 derivatives and analogs.

5.2 EXPRESSION OF THE C4-2 GENES

The nucleotide sequence coding for a C4-2 protein or a functionally active analog or fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native C+b 4-+b 2 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In specific embodiments, the human C4-2 gene is expressed, or a sequence encoding a functionally active portion of human C4-2. In yet another embodiment, a fragment of C+b 4-+b 2 comprising a domain of the C4-2 protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a C4-2 protein or peptide fragment may be regulated by a second nucleic acid sequence so that the C4-2 protein or peptide is expressed in a host transformed with the recombinant DNA molecule. For example, expression of a C4-2 protein may be controlled by any promoter/enhancer element known in the art. Promoters which may be used to control C+b 4-+b 2 expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to a C4-2-encoding nucleic acid, one or more origins of replication, and, optionally, one or more selectable markers (e.g., an antibiotic resistance gene).

In a specific embodiment, an expression construct is made by subcloning a C+b 4-+b 2 coding sequence into the EcoRI restriction site of each of the three pGEX vectors (Glutathione S-Transferase expression vectors; Smith and Johnson, 1988, Gene 7:31–40). This allows for the expression of the C4-2 protein product from the subclone in the correct reading frame.

Expression vectors containing C+b 4-+b 2 gene inserts can be identified by three general approaches: (a) nucleic acid hybridization, (b) presence or absence of "marker" gene functions, and (c) expression of inserted sequences. In the first approach, the presence of a C+b 4-+b 2 gene inserted in an expression vector can be detected by nucleic acid hybridization using probes comprising sequences that are homologous to an inserted C+b 4-+b 2 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a C+b 4-+b 2 gene in the vector. For example, if the C+b 4-+b 2 gene is inserted within the marker gene sequence of the vector, recombinants containing the C+b 4-+b 2 insert can be identified by the absence of the marker gene function. In the third approach, recombinant expression vectors can be identified by assaying the C4-2 product expressed by the recombinant. Such assays can be based, for example, on the physical or functional properties of the C4-2 protein in in vitro assay systems, e.g., binding with anti-C4-2 antibody, promotion of cell proliferation.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered C4-2 protein may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other specific embodiments, the C4-2 protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

5.3 IDENTIFICATION AND PURIFICATION OF THE C4-2 GENE PRODUCTS

In particular aspects, the invention provides amino acid sequences of C4-2, preferably human C4-2, and fragments and derivatives thereof which comprise an antigenic determinant (i.e., can be recognized by an antibody) or which are otherwise functionally active, as well as nucleic acid sequences encoding the foregoing. "Functionally active" C4-2 material as used herein refers to that material displaying one or more known functional activities associated with a full-length (wild-type) C4-2 protein, e.g., inhibition of cell proliferation, binding to a C4-2 substrate or C4-2 binding partner, antigenicity (binding to an anti-C4-2 antibody), immunogenicity, etc.

In specific embodiments, the invention provides fragments of a C4-2 protein consisting of at least 6 amino acids, 10 amino acids, 50 amino acids, or of at least 75 amino acids. In other embodiments, the proteins comprise or consist essentially of a C4-2 carboxy (C)-terminal domain 3, C4-2 C-terminal domain 2, C4-2 C-terminal domain 1, or any combination of the foregoing, of a C4-2 protein. Fragments, or proteins comprising fragments, lacking some or all of the foregoing regions of a C4-2 protein are also provided. Nucleic acids encoding the foregoing are provided.

Once a recombinant which expresses the C+b 4-+b 2 gene sequence is identified, the gene product can be analyzed. This is achieved by assays based on the physical or functional properties of the product, including radioactive labelling of the product followed by analysis by gel electrophoresis, immunoassay, etc.

Once the C4-2 protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, once a C4-2 protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In another alternate embodiment, native C4-2 proteins can be purified from natural sources, by standard methods such as those described above (e.g., immunoaffinity purification).

In a specific embodiment of the present invention, such C4-2 proteins, whether produced by recombinant DNA techniques or by chemical synthetic methods or by purification of native proteins, include but are not limited to those containing, as a primary amino acid sequence, all or part of the amino acid sequence, as well as fragments and other derivatives, and analogs thereof, including proteins homologous thereto.

5.4 STRUCTURE OF THE C4-2 GENE AND PROTEIN

The structure of the C+b 4-+b 2 gene and protein can be analyzed by various methods known in the art.

5.4.1 GENETIC ANALYSIS

The cloned DNA or cDNA corresponding to the C+b 4-+b 2 gene can be analyzed by methods including but not limited to Southern hybridization (Southern, E. M., 1975, J. Mol. Biol. 98:503–517), Northern hybridization (see e.g., Freeman et al., 1983, Proc. Natl. Acad. Sci. U.S.A. 80:4094–4098), restriction endonuclease mapping (Sambrook et al., 1989, Molecular Cloning, A Laboratory Manual, 2d Ed., Cold Spring Harbor Laboratory Press, Cold Spring Harbor, N.Y.), and DNA sequence analysis. Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with a C+b 4-+b 2-specific probe can allow the detection of the C+b 4-+b 2 gene in DNA from various cell types. Methods of amplification other than PCR are commonly known and can also be employed.

In one embodiment, Southern hybridization can be used to determine the genetic linkage of C4-2. Northern hybridization analysis can be used to determine the expression of the C+b 4-+b 2 gene. Various cell types, at various states of development or activity can be tested for C+b 4-+b 2 expression. The stringency of the hybridization conditions for both Southern and Northern hybridization can be manipulated to ensure detection of nucleic acids with the desired degree of relatedness to the specific C+b 4-+b 2 probe used. Modifications of these methods and other methods commonly known in the art can be used.

Restriction endonuclease mapping can be used to roughly determine the genetic structure of the C+b 4-+b 2 gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2 PROTEIN ANALYSIS

The amino acid sequence of the C4-2 protein can be derived by deduction from the DNA sequence, or alternatively, by direct sequencing of the protein, e.g., with an automated amino acid sequencer.

The C4-2 protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the C4-2 protein and the corresponding regions of the gene sequence which encode such regions.

Secondary, structural analysis (Chou, P. and Fasman, G., 1974, Biochemistry 13:222) can also be done, to identify regions of C4-2 that assume specific secondary structures.

Manipulation, translation, and secondary structure prediction, open reading frame prediction and plotting, as well as determination of sequence homologies, can also be accomplished using computer software programs available in the art.

Other methods of structural analysis can also be employed. These include but are not limited to X-ray crystallography (Engstom, A., 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5 GENERATION OF ANTIBODIES TO C4-2 PROTEINS AND DERIVATIVES THEREOF

According to the invention, C4-2 protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In a specific embodiment, antibodies to a human C4-2 protein are produced. In another embodiment, antibodies to a domain of a C4-2 protein are produced. In a specific embodiment, fragments of a C4-2 protein identified as hydrophilic are used as immunogens for antibody production.

Various procedures known in the art may be used for the production of polyclonal antibodies to a C4-2 protein or derivative or analog. For the production of antibody, various host animals can be immunized by injection with the native C4-2 protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a C4-2 protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for C4-2 together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce C4-2-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for C4-2 proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a C4-2 protein, one may assay generated hybridomas for a product which binds to a C4-2 fragment containing such domain. For selection of an antibody that specifically binds a first C4-2 homolog but which does not specifically bind a different C4-2 homolog, one can select on the basis of positive binding to the first C4-2 homolog and a lack of binding to the second C4-2 homolog.

Antibodies specific to a domain of a C4-2 protein are also provided.

The foregoing antibodies can be used in methods known in the art relating to the localization and activity of the C4-2 protein sequences of the invention, e.g., for imaging these proteins, measuring levels thereof in appropriate physiological samples, in diagnostic methods, etc.

In another embodiment of the invention (see infra), anti-C4-2 antibodies and fragments thereof containing the binding domain are Therapeutics.

5.6 C4-2 PROTEINS, DERIVATIVES AND ANALOGS

The invention further relates to C4-2 proteins, and derivatives (including but not limited to fragments) and analogs of C4-2 proteins. Nucleic acids encoding C4-2 protein derivatives and protein analogs are also provided. In one embodiment, the C4-2 proteins are encoded by the C4-2 nucleic acids described in Section 5.1 supra. In particular aspects, the proteins, derivatives, or analogs are of C4-2 proteins of animals, e.g., fly, frog, mouse, rat, pig, cow, dog, monkey, human, or of plants.

The production and use of derivatives and analogs related to C4-2 are within the scope of the present invention. In a specific embodiment, the derivative or analog is functionally active, i.e., capable of exhibiting one or more functional activities associated with a full-length, wild-type C4-2 protein. As one example, such derivatives or analogs which have the desired immunogenicity or antigenicity can be used, for examples in immunoassays, for immunization, for inhibition of C4-2 activity, etc. Derivatives or analogs that retain, or alternatively lack or inhibit, a desired C4-2 property of interest (e.g., binding to C4-2 binding partner, promotion of cell proliferation) can be used as inducers, or inhibitors, respectively, of such property and its physiological correlates. A specific embodiment relates to a C4-2 fragment that can be bound by an anti-C4-2 antibody. Derivatives or analogs of C4-2 can be tested for the desired activity by procedures known in the art, including but not limited to the assays described in Sections 5.7 and 5.9.

In particular, C4-2 derivatives can be made by altering C+b 4-+b 2 sequences by substitutions, additions or deletions that provide for functionally equivalent molecules. Due to the degeneracy of nucleotide coding sequences, other DNA sequences which encode substantially the same amino acid sequence as a C+b 4-+b 2 gene may be used in the practice of the present invention. These include but are not limited to nucleotide sequences comprising all or portions of C+b 4-+b 2 genes which are altered by the substitution of different codons that encode a functionally equivalent amino acid residue within the sequence, thus producing a silent change. Likewise, the C4-2 derivatives of the invention include, but are not limited to, those containing, as a primary amino acid sequence, all or part of the amino acid sequence of a C4-2 protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a C4-2 protein consisting of at least 10 (continuous) amino acids of the C4-2 protein is provided. In other embodiments, the fragment consists of at least 20 or 50 amino acids of the C4-2 protein. In specific embodiments, such fragments are not larger than 35, 100 or 200 amino acids. Derivatives or analogs of C4-2 include but are not limited to those molecules comprising regions that are substantially homologous to C4-2 or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding C+b 4-+b 2 sequence, under stringent, moderately stringent, or nonstringent conditions.

The C4-2 derivatives and analogs of the invention can be produced by various methods known in the art. The manipulations which result in their production can occur at the gene or protein level. For example, the cloned C+b 4-+b 2 gene sequence can be modified by any of numerous strategies known in the art (Sambrook et al., 1989, Molecular Cloning, A Laboratory Manual, 2d Ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of C4-2, care should be taken to ensure that the modified gene remains within the same translational reading frame as C4-2, uninterrupted by translational stop signals, in the gene region where the desired C4-2 activity is encoded.

Additionally, the C4-2 -encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), etc.

Manipulations of the C4-2 sequence may also be made at the protein level. Included within the scope of the invention are C4-2 protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of C4-2 can be chemically synthesized. For example, a peptide corresponding to a portion of a C4-2 protein which comprises the desired domain (see Section 5.6.1), or which mediates the desired activity in vitro, can be synthesized by use of a peptide synthesizer. Furthermore, if desired, nonclassical amino acids or chemical amino acid analogs can be introduced as a substitution or addition into the C4-2 sequence. Non-classical amino acids include but are not limited to the D-isomers of the common amino acids, $\alpha$-amino isobutyric acid, 4-aminobutyric acid, Abu, 2-amino butyric acid, $\gamma$-Abu, $\epsilon$-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, $\beta$-alanine, fluoro-amino acids, designer amino acids such as $\beta$-methyl amino acids, C$\alpha$-methyl amino acids, N$\alpha$-methyl amino acids, and amino acid analogs in general. Furthermore, the amino acid can be D (dextrorotary) or L (levorotary).

In a specific embodiment, the C4-2 derivative is a chimeric, or fusion, protein comprising a C4-2 protein or fragment thereof (preferably consisting of at least a domain or motif of the C4-2 protein, or at least 10 amino acids of the C4-2 protein) joined at its amino- or carboxy-terminus via a peptide bond to an amino acid sequence of a different protein. In one embodiment, such a chimeric protein is produced by recombinant expression of a nucleic acid encoding the protein (comprising a C4-2 -coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of C+b 4-+b 2 fused to any heterologous protein-encoding sequences may be constructed. A specific embodiment relates to a chimeric protein comprising a fragment of C4-2 of at least six amino acids.

In another specific embodiment, the C4-2 derivative is a molecule comprising a region of homology with a C4-2 protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to a C4-2 domain (see Section 5.6.1) or a portion thereof.

Other specific embodiments of derivatives and analogs are described in the subsection below and example sections infra.

5.6.1 DERIVATIVES OF C4-2 CONTAINING ONE OR MORE DOMAINS OF THE PROTEIN

In a specific embodiment, the invention relates to C4-2 derivatives and analogs, in particular C4-2 fragments and derivatives of such fragments, that comprise, or alternatively consist of, one or more domains of a C4-2 protein.

A specific embodiment relates to molecules comprising specific fragments of C4-2 that are those fragments in the respective C4-2 protein most homologous to specific fragments of a human or mouse C4-2 protein. A fragment comprising a domain of a C4-2 homolog can be identified by protein analysis methods as described in Sections 5.3.2 or 6.

In another specific embodiment, a molecule is provided that comprises one or more domains (or functional portion thereof) of a C4-2 protein but that also lacks one or more domains (or functional portion thereof) of a C4-2 protein. In another embodiment, a molecule is provided that comprises one or more domains (or functional portion thereof) of a C4-2 protein, and that has one or more mutant (e.g., due to deletion or point mutation(s)) domains of a C4-2 protein (e.g., such that the mutant domain has decreased function).

5.7 ASSAYS OF C4-2 PROTEINS, DERIVATIVES AND ANALOGS

The functional activity of C4-2 proteins, derivatives and analogs can be assayed by various methods.

For example, in one embodiment, where one is assaying for the ability to bind or compete with wild-type C4-2 for binding to anti-C4-2 antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where a C4-2 -binding protein is identified, the binding can be assayed, e.g., by means well-known in the art. In another embodiment, physiological correlates of C4-2 binding to its substrates (signal transduction) can be assayed.

In another embodiment, in insect or other model systems, genetic studies can be done to study the phenotypic effect of a C+b 4-+b 2 mutant that is a derivative or analog of wild-type C4-2 (see Section 6, infra).

In addition, assays that can be used to detect or measure the ability to inhibit, or alternatively promote, cell proliferation are described in Section 5.9.

Other methods will be known to the skilled artisan and are within the scope of the invention.

5.8 THERAPEUTIC USES

The invention provides for treatment or prevention of various diseases and disorders by administration of a therapeutic compound (termed herein "Therapeutic"). Such "Therapeutics" include but are not limited to: C4-2 proteins and analogs and derivatives (including fragments) thereof (e.g., as described hereinabove); antibodies thereto (as described hereinabove); nucleic acids encoding the C4-2 proteins, analogs, or derivatives (e.g., as described hereinabove); C+b 4-+b 2 antisense nucleic acids, and C4-2 agonists and antagonists. Disorders involving tumorigenesis or cell overproliferation are treated or prevented by administration of a Therapeutic that promotes C+b 4-+b 2 function. Disorders in which cell proliferation is deficient or is desired are treated or prevented by administration of a Therapeutic that inhibits C4-2 function. See details in the subsections below.

Generally, is is preferred to administer a product of a species origin or species reactivity (in the case of antibodies) that is the same as that of the recipient. Thus, in a preferred embodiment, a human C4-2 protein, derivative, or analog, or nucleic acid, or an antibody to a human C4-2 protein, is therapeutically or prophylactically administered to a human patient.

Additional descriptions and sources of Therapeutics that can be used according to the invention are found in Sections 5.1 through 5.7 supra herein.

5.8.1 TREATMENT AND PREVENTION OF DISORDERS INVOLVING OVERPROLIFERATION OF CELLS

Diseases and disorders involving cell overproliferation are treated or prevented by administration of a Therapeutic that promotes C4-2 function. Examples of such a Therapeutic include but are not limited to nucleic acids encoding C4-2 under the control of a strong inducible promoter, particularly that are active in inhibiting cell proliferation (e.g., as demonstrated in In vitro assays or in animal models or in Drosophila). Other Therapeutics that can be used, e.g., C4-2, can be identified using in vitro assays or animal models, examples of which are described infra.

In specific embodiments, Therapeutics that promote C4-2 function are administered therapeutically (including prophylactically): (1) in diseases or disorders involving an decreased (relative to normal or desired) level of C4-2 protein or function, for example, in patients where C4-2 protein is underexpressed, genetically defective, or biologically hypoactive; or (2) in diseases or disorders wherein in vitro (or in vivo) assays (see infra) indicate the utility of C4-2 agonist administration. The decreased level in C4-2 protein or function can be readily detected, e.g., by obtaining a patient tissue sample (e.g., from biopsy tissue) and assaying it in vitro for RNA or protein levels, structure and/or activity of the expressed C4-2 RNA or protein. Many methods standard in the art can be thus employed, including but not limited to immunoassays to detect and/or visualize C4-2 protein (e.g., Western blot, immunoprecipitation followed by sodium dodecyl sulfate polyacrylamide gel electrophoresis, immunocytochemistry, etc.) and/or hybridization assays to detect C4-2 expression by detecting and/or visualizing C4-2 mRNA (e.g., Northern assays, dot blots, in situ hybridization, etc.), etc.

Diseases and disorders involving cell overproliferation that can be treated or prevented include but are not limited to malignancies, premalignant conditions (e.g., hyperplasia, metaplasia, dysplasia), benign tumors, hyperproliferative disorders, benign dysproliferative disorders, etc. Examples of these are detailed below.

5.8.1.1 MALIGNANCIES

Malignancies and related disorders that can be treated or prevented by administration of a Therapeutic that promotes C4-2 function include but are not limited to those listed in Table 1 (for a review of such disorders, see Fishman et al., 1985, *Medicine,* 2d Ed., J. B. Lippincott Co., Philadelphia):

TABLE 1

MALIGNANCIES AND RELATED DISORDERS

Leukemia
acute leukemia acute lymphocytic leukemia
acute lymphoblastic leukemia
acute myelocytic leukemia
myeloblastic
myelogenous
promyelocytic
myelomonocytic
monocytic
erythroleukemia
chronic leukemia chronic myelocytic (granulocytic) leukemia
chronic myelogenous leukemia
chronic lymphocytic leukemia
Polycythemia vera
Lymphoma Hodgkin's disease
non-Hodgkin's disease
Multiple myeloma
Waldenström's macroglobulinemia
Heavy chain disease
Solid tumors
sarcomas and carcinomas adenocarcinoma
fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon carcinoma
colorectal adenocarcinoma
colon tumor metastatic to brain
lung carcinoma
pancreatic cancer
breast cancer
ovarian cancer
prostate cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma TABLE 1-continued

MALIGNANCIES AND RELATED DISORDERS

Wilms' tumor
cervical cancer
uterine cancer
testicular tumor
lung carcinoma
small cell lung carcinoma
bladder carcinoma
epithelial carcinoma
glioblastoma
glioma
astrocytoma
medulloblastoma
craniopharyngioma
ependymoma
pinealoma
hemangioblastoma
acoustic neuroma
oligodendroglioma
meningioma
melanoma
neuroblastoma
retinoblastoma In specific embodiments, malignancy or dysproliferative changes (such as metaplasias and dysplasias), or hyperproliferative disorders, are treated or prevented in the brain, breast colon, prostate, lung, or skin. In other specific embodiments, carcinoma, melanoma, or leukemia is treated or prevented.

5.8.1.2 PREMALIGNANT CONDITIONS

The Therapeutics of the invention that agonize and promote C+b 4-+b 2 activity can also be administered to treat premalignant conditions and to prevent progression to a neoplastic or malignant state, including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology,* 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/ therapeutic administration of a Therapeutic that inhibits C4-2 function. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112–113) etc.)

In another specific embodiment, a Therapeutic of the invention is administered to a human patient to prevent progression to brain, breast, colon, prostate, lung, or skin. In other specific embodiments, carcinoma, melanoma, or leukemia is treated or prevented.

5.8.1.3 GENE THERAPY

In a specific embodiment, anti-sense nucleic acids complementary to a sequence encoding a C4-2 protein or functional derivative thereof, are administered to inhibit C4-2 function, by way of gene therapy. Gene therapy refers to therapy performed by the administration of a nucleic acid to a subject. In this embodiment of the invention, the antisense nucleic acid mediates a therapeutic effect by inhibiting C4-2 transcription and translation.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, N.Y.

In one embodiment, the Therapeutic comprises an C4-2 sense or antisense nucleic acid that is part of an expression vector that expresses a C4-2 protein or fragment or chimeric protein thereof in a suitable host. In particular, such a nucleic acid has a promoter operably linked to the C4-2 coding region, said promoter being inducible or constitutive, and, optionally, tissue-specific. In another particular embodiment, a nucleic acid molecule is used in which the C4-2 coding sequences and any other desired sequences are flanked by regions that promote homologous recombination at a desired site in the genome, thus providing for intrachromosomal expression of the C4-2 nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO 92/20316 dated Nov. 26, 1992 (Findeis et al.); WO 93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. U.S.A. 86:8932–8935; Zijlstra et al., 1989, Nature 342:435–438).

In a specific embodiment, a viral vector that contains the C+b 4-+b 2 nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The C+b 4-+b 2 nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234.

Adeno-associated virus (AAV) has also been proposed for use in gene therapy (Walsh et al., 1993, Proc. Soc. Exp. Biol. Med. 204:289–300.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a C+b 4-+b 2 nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, 1992, Cell 71:973–985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. U.S.A. 79:3608–3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods that can be adapted for use to deliver a nucleic acid encoding a C4-2 protein or functional derivative thereof are described in Section 5.8.2.2.2.

5.8.2 TREATMENT AND PREVENTION OF HYPERPROLIFERATIVE AND DYSPROLIFERATIVE DISORDERS

Diseases and disorders involving an increase in cell proliferation (growth) or in which cell proliferation is otherwise undesirable, are treated or prevented by administration of a Therapeutic that antagonizes (inhibits) C4-2 function. Therapeutics that can be used include but are not limited to anti-C4-2 antibodies (and fragments and derivatives thereof containing the binding region thereof), C+b 4-+b 2 antisense nucleic acids, and C+b 4-+b 2 nucleic acids that are dysfunctional (e.g., due to a heterologous (non-C+b 4-+b 2 sequence) insertion within the C+b 4-+b 2 coding sequence) that are used to "knockout" endogenous C+b 4-+b 2 function by homologous recombination (see, e.g., Capecchi, 1989, Science 244:1288–1292). In a specific embodiment of the invention, a nucleic acid containing a portion of a C+b 4-+b 2 gene in which C+b 4-+b 2 sequences flank (are both 5' and 3' SEQ ID NO: to) a different gene sequence, is used, as a C4-2 antagonist, to promote C+b 4-+b 2 inactivation by homologous recombination (see also Koller and Smithies, 1989, Proc. Natl. Acad. Sci. U.S.A. 86:8932–8935; Zijlstra et al., 1989, Nature 342:435–438). Other Therapeutics that inhibit C4-2 function can be identified by use of known convenient in vitro assays, e.g., based on their ability to inhibit binding of C4-2 to another protein or inhibit any known C4-2 function, as preferably assayed in vitro or in cell culture, although genetic assays (e.g., in Drosophila) may also be employed. Preferably, suitable in vitro or in vivo assays, are utilized to determine the effect of a specific Therapeutic and whether its administration is indicated for treatment of the affected tissue.

In specific embodiments, Therapeutics that inhibit C4-2 function are administered therapeutically (including prophylactically): (1) in diseases or disorders involving an increased (relative to normal or desired) level of C4-2 protein or function, for example, in patients where C4-2 protein is overactive or overexpressed; or (2) in diseases or disorders wherein in vitro (or in vivo) assays (see infra) indicate the utility of C4-2 antagonist administration. The increased levels in C4-2 protein or function can be readily detected, e.g., by quantifying protein and/or RNA, by obtaining a patient tissue sample (e.g., from biopsy tissue) and assaying it in vitro for RNA or protein levels, structure and/or activity of the expressed C4-2 RNA or protein. Many methods standard in the art can be thus employed, including but not limited to immunoassays to detect and/or visualize C4-2 protein (e.g., Western blot, immunoprecipitation followed by sodium dodecyl sulfate polyacrylamide gel electrophoresis, immunocytochemistry, etc.) and/or hybridization assays to detect C4-2 expression by detecting and/or visualizing respectively C4-2 mRNA (e.g., Northern assays, dot blots, in situ hybridization, etc.), etc.

In other embodiments, chemical mutagenesis, or homologous recombination with an insertionally inactivated C4-2 gene (see Capecchi, 1989, Science 244:1288–1292 and Section 5.14 infra) can be carried out to reduce or destroy endogenous C4-2 function, in order to decrease cell proliferation. Suitable methods, modes of administration and compositions, that can be used to inhibit C4-2 function are described in Sections 5.8.2 through 5.8.2.1.2, above.

In an embodiment of the invention, a Therapeutic that inhibits C4-2 activity is used to treat or prevent hyperproliferative or benign dysproliferative disorders. Specific embodiments are directed to treatment or prevention of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

5.8.2.1 ANTISENSE REGULATION OF C4-2 EXPRESSION

In a specific embodiment, C4-2 function is inhibited by use of C+b 4-+b 2 antisense nucleic acids. The present invention provides the therapeutic or prophylactic use of nucleic acids of at least six nucleotides that are antisense to a gene or cDNA encoding C4-2 or a portion thereof. A C+b 4-+b 2 "antisense" nucleic acid as used herein refers to a nucleic acid capable of hybridizing to a portion of a C+b 4-+b 2 RNA (preferably mRNA) by virtue of some sequence complementarity. The antisense nucleic acid may be complementary to a coding and/or noncoding region of a C+b 4-+b 2 mRNA. Such antisense nucleic acids have utility as Therapeutics that inhibits C4-2 function, and can be used in the treatment or prevention of disorders as described supra in Section 5.8.2 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the C+b 4-+b 2 antisense nucleic acids provided by the instant invention can be used to prevent tumors or other forms of aberrant cell proliferation.

The invention further provides pharmaceutical compositions comprising an effective amount of the C+b 4-+b 2 antisense nucleic acids of the invention in a pharmaceutically acceptable carrier, as described infra.

In another embodiment, the invention is directed to methods for inhibiting the expression of a C+b 4-+b 2 nucleic acid sequence in a prokaryotic or eukaryotic cell comprising providing the cell with an effective amount of a composition comprising an C+b 4-+b 2 antisense nucleic acid of the invention.

C+b 4-+b 2 antisense nucleic acids and their uses are described in detail below.

5.8.2.1.1 C4-2 ANTISENSE NUCLEIC ACIDS

The C+b 4-+b 2 antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a C+b 4-+b 2 antisense oligonucleotide is provided, preferably of single-stranded DNA. The oligonucleotide may be modified at any position on its structure with substituents generally known in the art.

The C4-2 antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, the C+b 4-+b 2 antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the C+b 4-+b 2 antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the C+b 4-+b 2 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the C4-2 antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' SEQ ID NO: long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a C+b 4-+b 2 gene, preferably a human C+b 4-+b 2 gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded C4-2 antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a C+b 4-+b 2 RNA it may contain and still form a stable duplex (or triplex, as the case may be). One skilled in the art can ascertain a tolerable degree of mismatch by use of standard procedures to determine the melting point of the hybridized complex.

5.8.2.1.2 THERAPEUTIC USE OF C4-2 ANTISENSE NUCLEIC ACIDS

The C+b 4-+b 2 antisense nucleic acids can be used to treat (or prevent) disorders of a cell type that expresses, or preferably overexpresses, C+b 4-+b 2. In a specific embodiment, such a disorder is a growth deficiency. In a preferred embodiment, a single-stranded DNA antisense C4-2 oligonucleotide is used.

Cell types which express or overexpress C+b 4-+b 2 RNA can be identified by various methods known in the art. Such methods include but are not limited to hybridization with a C+b 4-+b 2 specific nucleic acid (e.g. by Northern hybridization, dot blot hybridization, in situ hybridization), observing the ability of RNA from the cell type to be translated in vitro into C4-2, immunoassay, etc. In a preferred aspect, primary tissue from a patient can be assayed for C4-2 expression prior to treatment, e.g., by immunocytochemistry or in situ hybridization.

Pharmaceutical compositions of the invention (see Section 5.10), comprising an effective amount of a C+b 4-+b 2 antisense nucleic acid in a pharmaceutically acceptable carrier, can be administered to a patient having a disease or disorder which is of a type that expresses or overexpresses C+b 4-+b 2 RNA or protein.

The amount of C+b 4-+b 2 antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising C+b 4-+b 2 antisense nucleic acids are administered via liposomes, microparticles, or microcapsules. In various embodiments of the invention, it may be useful to use such compositions to achieve sustained release of the C+b 4-+b 2 antisense nucleic acids. In a specific embodiment, it may be desirable co utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

Additional methods that can be adapted for use to deliver a C+b 4-+b 2 antisense nucleic acid are described in Section 5.8.1.4.

5.9 DEMONSTRATION OF THERAPEUTIC OR PROPHYLACTIC UTILITY

The Therapeutics of the invention are preferably tested in vitro, and then in vivo for the desired therapeutic or prophylactic activity, prior to use in humans.

For example, In vitro assays which can be used to determine whether administration of a specific Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.8.1 through 5.8.3 infra.

In another specific embodiment, a Therapeutic is indicated for use in treating cell injury or a degenerative disorder (see Section 5.8.2) which exhibits in vitro promotion of growth/proliferation of cells of the affected patient type. Regarding nervous system disorders, see also Section 5.8.2.1 for assays that can be used.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the cell type upon which an effect is desired, according to the present invention.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.10 THERAPEUTIC/PROPHYLACTIC ADMINISTRATION AND COMPOSITIONS

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described in Sections 5.8.1.4 and 5.8.2.2 above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol.

Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or preneoplastic tissue.

In another embodiment, the Therapeutic can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. U.S.A. 88:1864–1868), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.10.1 TREATMENT AND PREVENTION OF HYPOPROLIFERATIVE DISORDERS

Diseases and disorders involving decreased cell proliferation or in which cell proliferation is desired for treatment or prevention, and that can be treated or prevented by inhibiting C4-2 function, include but are not limited to degenerative disorders, growth deficiencies, hypoproliferative disorders, physical trauma, lesions, and wounds; for example, to promote wound healing, or to promote regeneration in degenerated, lesioned or injured tissues, etc. In a specific embodiment, nervous system disorders are treated. In another specific embodiment, a disorder that is not of the nervous system is treated.

Lesions which may be treated according to the present invention include but are not limited to the following lesions:

(i) traumatic lesions, including lesions caused by physical injury or associated with surgery;

(ii) ischemic lesions, in which a lack of oxygen results in cell Injury or death, e.g., myocardial or cerebral infarction or ischemia, or spinal cord infarction or ischemia;

(iii) malignant lesions, in which cells are destroyed or injured by malignant tissue;

(iv) infectious lesions, in which tissue is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which tissue is destroyed or injured as a result of a degenerative process, including but not limited to nervous system degeneration associated with Parkinson's disease, Alzheimer's disease, Huntington's chorea, or amyotrophic lateral sclerosis;

(vi) lesions associated with nutritional diseases or disorders, in which tissue is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) lesions associated with systemic diseases including but not limited to diabetes or systemic lupus erythematosus;

(viii) lesions caused by toxic substances including alcohol, lead, or other toxins; and (ix) demyelinated lesions of the nervous system, in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Nervous system lesions which may be treated in a patient (including human and non-human mammalian patients) according to the invention include but are not limited to the lesions of either the central (including spinal cord, brain) or peripheral nervous systems.

Therapeutics which are useful according to this embodiment of the invention for treatment of a disorder may be selected by testing for biological activity in promoting the survival or differentiation of cells (see also Section 5.9). For example, in a specific embodiment relating to therapy of the nervous system, a Therapeutic which elicits one of the following effects may be useful according to the invention:

(i) increased sprouting of neurons in culture or in vivo;

(ii) increased production of a neuron-associated molecule in culture or in vivo, e.g., choline acetyltransferase or acetylcholinesterase with respect to motor neurons; or (iii) decreased symptoms of neuron dysfunction in vivo. Such effects may be measured by any method known in the art. In preferred, non-limiting embodiments, increased sprouting of neurons may be detected by methods set forth in Pestronk et al. (1980, Exp. Neurol. 70:65–82) or Brown et al. (1981, Ann. Rev. Neurosci. 4:17–42); and increased production of neuron-associated molecules may be measured by bioassay, enzymatic assay, antibody binding, Northern blot assay, etc., depending on the molecule to be measured.

5.11 ADDITIONAL USE OF DECREASED C4-2 FUNCTION TO PROMOTE INCREASED GROWTH

Inhibition of C4-2 function (e.g., by administering a compound that inhibits C4-2 function as described in Sections 5.8.2 through 5.8.2.1.2 above), has utility that is not limited to therapeutic or prophylactic applications. For example, C4-2 function can be inhibited in order to increase growth of animals (e.g., cows, horses, pigs, goats, deer, chickens) and plants (particularly edible plants, e.g., tomatoes, melons, lettuce, carrots, potatoes, and other vegetables), particularly those that are food or material sources. In an embodiment in which a C4-2 antisense nucleic acid is under the control of a tissue-specific promoter, the invention can be used in plants or animals to increase growth where desired (e.g., in the fruit or muscle). For example, a C+b 4-+b 2 antisense nucleic acid under the control of a temperature-sensitive promoter can be administered to a plant or animal, and the desired portion of the (or the entire) plant or animal can be subjected to heat in order to induce C4-2 antisense nucleic acid production, resulting in decreased C4-2 expression, and resulting cell proliferation. Methods to make plants recombinant are commonly known in the art and can be used. Regarding methods of plant transformation (e.g., for transformation with a C+b 4-+b 2 antisense nucleic acid), see e.g., Valvekens et al., 1988, Proc. Natl. Acad. Sci. U.S.A. 85:5536–5540. Regarding methods of targeted gene inactivation in plants (e.g., to inactivate C+b 4-+b 2 ), see e.g., Miao and Lam, 1995, The Plant J. 7:359–365.

Inhibition of C4-2 function can also have uses in vitro, e.g., to expand cells in vitro, including but not limited to stem cells, progenitor cells, muscle cells, fibroblasts, liver cells, etc., e.g., to grow cells/tissue in vitro prior to administration to a patient (preferably a patient from which the cells were derived), etc.

5.12 DIAGNOSIS AND SCREENING

C4-2 proteins, analogues, derivatives, and subsequences thereof, C+b 4-+b 2 nucleic acids (and sequences complementary thereto), anti-C4-2antibodies, have uses in diagnostics. Such molecules can be used in assays, such as immunoassays, to detect, prognose, diagnose, or monitor various conditions, diseases, and disorders affecting C4-2 expression, or monitor the treatment thereof. In particular, such an immunoassay is carried out by a method comprising contacting a sample derived from a patient with an anti-C4-2 antibody under conditions such that immunospecific binding can occur, and detecting or measuring the amount of any immunospecific binding by the antibody. In a specific aspect, such binding of antibody, in tissue sections, can be used to detect aberrant C4-2 localization or aberrant (e.g., low or absent) levels of C4-2. In a specific embodiment, antibody to C4-2 can be used to assay in a patient tissue or serum sample for the presence of C4-2 where an aberrant level of C4-2 is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

C+b 4-+b 2 genes and related nucleic acid sequences and subsequences, including complementary sequences, can also be 35 used in hybridization assays. C4-2 nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in C4-2 expression and/or activity as described supra In particular, such a hybridization assay is carried out by a method comprising contacting a sample containing nucleic acid with a nucleic acid probe capable of hybridizing to C+b 4-+b 2 DNA or RNA, under conditions such that hybridization can occur, and detecting or measuring any resulting hybridization.

In specific embodiments, diseases and disorders involving overproliferation of cells can be diagnosed, or their suspected presence can be screened for, or a predisposition to develop such disorders can be detected, by detecting increased levels of C4-2 protein, C4-2 RNA, or C4-2 functional activity or by detecting mutations in C4-2 RNA, DNA or protein (e.g., translocations in C4-2 nucleic acids, truncations in the C4-2 gene or protein, changes in nucleotide or amino acid sequence relative to wild-type C4-2) that cause increased expression or activity of C4-2. Such diseases and disorders include but are not limited to those described in Section 5.8.1 and its subsections. By way of example, levels of C4-2 protein can be detected by immunoassay, levels of C4-2 RNA can be detected by hybridization assays (e.g., Northern blots, dot blots), translocations and point mutations in C4-2 nucleic acids can be detected by Southern blotting, RFLP analysis, PCR using primers that preferably generate a fragment spanning at least most of the C4-2 gene, sequencing of the C4-2 genomic DNA or cDNA obtained from the patient, etc.

In a preferred embodiment, levels of C4-2 mRNA or protein in a patient sample are detected or measured, in which increased levels indicate that the subject has, or has a predisposition to developing, a malignancy or hyperproliferative disorder; in which the increased levels are relative to the levels present in an analogous sample from a portion of the body or from a subject not having the malignancy or hyperproliferative disorder, as the case may be.

In another specific embodiment, diseases and disorders involving a deficiency in cell proliferation or in which cell proliferation is desirable for treatment, are diagnosed, or their suspected presence can be screened for, or a predisposition to develop such disorders can be detected, by detecting decreased levels of C4-2 protein, C4-2 RNA, or C4-2 functional activity, or by detecting mutations in C4-2 RNA, DNA or protein (e.g., translocations in C4-2 nucleic acids, truncations in the gene or protein, changes in nucleotide or amino acid sequence relative to wild-type C4-2) that cause decreased expression or activity of C4-2. Such diseases and disorders include but are not limited to those described in Section 5.8.2 and its subsections. By way of example, levels of C4-2 protein, levels of C4-2 RNA, C4-2 binding activity, and the presence of translocations or point mutations can be determined as described above.

In a specific embodiment, levels of C4-2 mRNA or protein in a patient sample are detected or measured, in which decreased levels indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

Kits for diagnostic use are also provided, that comprise in one or more containers an anti-C4-2 antibody, and, optionally, a labeled binding partner to the antibody. Alternatively, the anti-C4-2 antibody can be labeled (with a detectable marker, e.g., a chemiluminescent, enzymatic, fluorescent, or radioactive moiety). A kit is also provided that comprises in one or more containers a nucleic acid probe capable of hybridizing to C+b 4-+b 2 RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of a C+b 4-+b 2 nucleic acid. A kit can optionally further comprise in a container a predetermined amount of a purified C4-2 protein or nucleic acid, e.g., for use as a standard or control.

5.13 SCREENING FOR C4-2 AGONISTS AND ANTAGONISTS

C+b 4-+b 2 nucleic acids, proteins, and derivatives also have uses in screening assays to detect molecules that specifically bind to C+b 4-+b 2 nucleic acids, proteins, or derivatives and thus have potential use as agonists or antagonists of C4-2, in particular, molecules that thus affect cell proliferation. In a preferred embodiment, such assays are performed to screen for molecules with potential utility as anti-cancer drugs or lead compounds for drug development. The invention thus provides assays to detect molecules that specifically bind to C+b 4-+b 2 nucleic acids, proteins, or derivatives. For example, recombinant cells expressing C4-2 nucleic acids can be used to recombinantly produce C4-2 proteins in these assays, to screen for molecules that bind to a C4-2 protein. Molecules (e.g., putative binding partners of C4-2 ) are contacted with the C4-2 protein (or fragment thereof) under conditions conducive to binding, and then molecules that specifically bind to the C4-2 protein are identified. Similar methods can be used to screen for molecules that bind to C4-2 derivatives or nucleic acids. Methods that can be used to carry out the foregoing are commonly known in the art.

By way of example, diversity libraries, such as random or combinatorial peptide or nonpeptide libraries can be screened for molecules that specifically bind to C4-2. Many libraries are known in the art that can be used, e.g., chemically synthesized libraries, recombinant (e.g., phage display libraries) and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. U.S.A. 90:10922–10926; Erb et al., 1994, Proc. Natl. Acad. Sci. U.S.A. 91:11422–11426; Houghten et al., 1992, Biotechniques 13:412; Jayawickreme et al., 1994, Proc. Natl. Acad. Sci. U.S.A. 91:1614–1618; Salmon et al., 1993, Proc. Natl. Acad. Sci. U.S.A. 90:11708–11712; PCT Publication No. WO 93/20242; and Brenner and Lerner, 1992, Proc. Natl. Acad. Sci. U.S.A. 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. U.S.A. 91:9022–9026.

By way of examples of nonpeptide libraries, a benzodiazepine library (see e.g., Bunin et al., 1994, Proc. Natl. Acad. Sci. U.S.A. 91:4708–4712) can be adapted for use. Peptoid libraries (Simon et al., 1992, Proc. Natl. Acad. Sci. U.S.A. 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. U.S.A. 91:11138–11142).

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. U.S.A. 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. U.S.A. 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and PCT Publication No. WO 94/18318.

In a specific embodiment, screening can be carried out by contacting the library members with a C4-2 protein (or nucleic acid or derivative) immobilized on a solid phase and harvesting those library members that bind to the protein (or nucleic acid or derivative). Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove.

In another embodiment, the two-hybrid system for selecting interacting proteins in yeast (Fields and Song, 1989, Nature 340:245–246; Chien et al., 1991, Proc. Natl. Acad. Sci. U.S.A. 88:9578–9582) can be used to identify molecules that specifically bind to a C4-2 protein or derivative.

5.14 ANIMAL MODELS

The invention also provides animal models. In one embodiment, animal models for diseases and disorders involving cell hypoproliferation (e.g., as described in Section 5.8.1) are provided. Such an animal can be initially produced by promoting homologous recombination between a C4-2 gene in its chromosome and an exogenous C4-2 gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally inactivated C+b 4-+b 2 gene, such that homologous recombination occurs, followed by injecting the ES cells into a blastocyst, and implanting the blastocyst into a foster mother, followed by the birth of the chimeric animal ("knockout animal") in which a C+b 4-+b 2 gene has been inactivated (see Capecchi, 1989, Science 244:1288–1292). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving cell hypoproliferation. Such animals can be used to screen for or test molecules for the ability to promote proliferation and thus treat or prevent such diseases and disorders.

In a different embodiment of the invention, transgenic animals that have incorporated and express a functional C+b 4-+b 2 gene have use as animal models of diseases and disorders involving cell hyperproliferation or malignancy. Such animals are expected to develop or be predisposed to developing diseases or disorders involving cell hyperproliferation (e.g., malignancy) and thus can have use as animal models of such diseases and disorders, e.g., to screen for or test molecules (e.g., potential anti-cancer therapeutics) for the ability to inhibit overproliferation (e.g., tumor formation) and thus treat or prevent such diseases or disorders.

6. EXAMPLE

ISOLATION AND CHARACTERIZATION OF A NOVEL C4-2 GENE

Specific markers are needed to recognize and diagnose brain tumors in early stages of tumorigenesis. This example describes the isolation of a novel gene, C+b 4-+b 2, that is overexpressed in normal brain tissue (NBT) and expressed at very low levels in glioblastoma multiforme tissue (GMT).

6.1 MATERIALS AND METHODS

6.1.1 HUMAN TISSUES AND CELL LINES

Various tumor samples of brain and non-brain tumors were procured from the tissue bank maintained by Pacific Northwest Cancer Foundation, Northwest Hospital and from sources at the Mayo Clinic in Minnesota. Brain tumor cell lines CCF-STTG1 (astrocytoma grade IV), SW 1783 (astrocytoma grade III), IMR-32 (neuroblastoma), D283 Med (medulloblastoma), Hs 683 (glioma), PFSK-1 (primitive neuroectodermal tumor) and DBTRG-05MG (glioblastoma multiforme) cell lines were purchased from ATCC (American Type Culture Collection, Rockville, Md.). Fetal normal human astrocytes (FNHA) were purchased from Clonetics (San Diego, Calif.). All the cell lines were cultured under the conditions recommended by ATCC or Clonetics.

6.1.2 DIFFERENTIAL DISPLAY-POLYMERASE CHAIN REACTION (DD-PCR)

The C+b 4-+b 2 gene was isolated using the Differential Display—Polymerase Chain Reaction (DD-PCR) technique. DD-PCR is a modified PCR technique first developed in 1992, Liang et al., 1992, Science 257:967–971; Liang et al., 1992, Cancer Research 52:6966–6968). DD-PCR technique has been modified and improved recently to increase PCR specificity and efficiency (Hadman et al., 1995, Anal. Chem. 226:383–386; Sehgal et al., 1996, Exp. Lung Res., 22:419–434).

Differentially expressed genes from NBT (Normal brain tissue) and GMT (Glioblastoma Multiforme Tissue) were isolated and cloned using the protocol of Hadman et al., supra. NBT and GMT were obtained from the same region of the brain. Total RNA was isolated using the GITC/CsCl$_2$ protocol described previously by Sambrook et al., 1989, supra. Five µg of total RNA was treated with DNaseI (Amersham, Arlington, Ill.) (2 units/µl) for 30 minutes at 37° C. RNA was then extracted and precipitated using 3M sodium acetate. First strand cDNA synthesis was then carried out using the Advantage 1st Strand cDNA synthesis kit from Clontech (Palo Alto, Calif.) and BT3-2 primer (5'T(T) 18NG3'). Approximately 125 ng of first strand cDNA synthesis product was used for carrying out the PCR reaction.

DD-PCR reaction was carried out using ($\gamma$P$^{32}$)end labelled BT-2 primer and BT8 (5'NTACTGATCCATGACA3' SEQ ID NO:3), BT10(5'NGCTGCTCTCATACT3' SEQ ID NO:4) or B12 (5'NTGATCTAAGGCACATA3' SEQ ID NO:5) primers using cDNA from NBT or GMT tissue in duplicate, and using the conditions of Hadman et al., supra. PCR products were then electrophoresed on a 6% sequencing gel. The bands that showed differential expression were then cut out and DNA was eluted. PCR was then carried as done for DD-PCR conditions using appropriate primers. PCR product was then cloned into PCRII vector from Invitrogen. Positive clones were screened by PCR and sequenced using the Sequenase version 2.0 sequencing kit (Amersham/USB, Arlington Heights, Ill.).

6.1.3 GENE-SPECIFIC RT-PCR

To confirm the differential expression of clones isolated by DD-PCR, a RT-PCR technique (Ikonomov et al., 1996, Biotechniques 20:1030–1042) was used. In brief 5 µg of total RNA was treated with DNaseI and first strand synthesis was carried out under the same conditions as described previously. First strand cDNA was used as template to carry out PCR using primers BT-63 (5'TGATCCATGACATTCAGTG3' SEQ ID NO:6) and BT-64 (5'GGAATGCAGAGTATTGAAG3' SEQ ID NO:7) specific for C4-2 ; primers BT41 (5'CTCAGTGTTAACGGATAAT3' SEQ ID NO:8) specific for D+b 2-+b 2, and primer BT42 (5'TGTTGAGAAGAGTACATCTT3' SEQ ID NO:9). D+b 1-+b 2 gene that is expressed in both NBT and GMT was used as an internal control. PCR for D+b 1-+b 2 was carried out using BT-59 (5'CGGAGCAATATGAAATGATCT3' SEQ ID NO:10) and BT-60 (5'GCAAATACAGCTCCTATTG3' SEQ ID NO:11). RT-PR was performed using Gene Amp PCR kit from Perkin Elmer (Branchburg, N.J.) under the following conditions: 4 µl of dNTP mix, 2 µl (100 ng/µl) each of D1-2 or C4-2 specific primers, 4 µl of 25 mM MgCl$_2$, 125 ng of cDNA template and 5 units of Amplitaq DNA polymerase. PCR conditions were performed as follows: 94° C., 50° C. and 72° C. for 1 minute each for 35 cycles. PCR product was then run on a 2% agarose gel. DNA was transferred on to MSI magnacharge membrane using the standard Southern Blotting conditions as described by Sambrook, supra. Membrane was prehybridized for 12 hours in Prehybridization buffer (Sambrook). Hybridization was done at 42° C. using C4-2, D1-2 or C4-2 specific probes. C4-2, D2-2 and D1-2 specific probes were prepared by multiprime labelling (Amersham Megaprime Labelling Kit): C4-2-(5'TTGTGCAAATACGATATGTTGCCTTAGGC ATATCTTTTGT3' SEQ ID NO:12), D2-2-(5'CCAAACTGGACATCAAGGAATTGCTACAC AGAAGAACCACCATCCAGGATAGAA3' SEQ ID NO:13) or D1-2-(5'TAGGCCTGACTGGCATTGTATTAGCAAAC TCAT-CACTAGA3' SEQ ID NO:14) specific primers were used. These primers are internal to the primers used for PCR and they do not carry any of the primer sequences used in the PCR. Primer sequences were checked for homologous sequences using DNA BLAST program prior to usage. Quantitation of the signal on Southern blot was carried out using Imagequant program of the Molecular Dynamics Phosphor Imager (Sunnyvale, Calif.). See Section 6.1.6, infra. This protocol was also used to quantitate expression of C4-2, C4-2 or D1-2 in brain tumor cell lines, FNHA and tumor tissues.

6.1.4 CLONING AND SEQUENCING OF C4-2

The DD-PCR product for clone C4-2 was about 250 bases long. It was cloned into the PCRII vector from Invitrogen (San Diego, Calif.). Clone C4-2 was sequenced using Sequenase 2.0 kit from Amersham. Using the 250 bp fragment, a human brain library and a 2.0 Kb insert was isolated. This clone was sequenced partially to confirm its identity. The database at the National Center for Biotechnology Information (NCBI; NIH, Bethesda, Md.) was searched for C4-2 homology with other sequences using the BLAST program.

6.1.5 NORTHERN BLOT ANALYSIS

To investigate the expression of C+b 4-+b 2 in brain and normal tissues, Multiple Tissue Blots (MTB) from Clonetech were used. These blots have 2 µg of pure polyA pure mRNA blotted onto them. MTBs were prehybridized in express hybridization buffer solution for 3–4 hours. Hybridization was done with a multiprime labelled 2.0 Kb C4-2 probe. After autoradiographic exposure, the probe was washed from the blot and then hybridized with human β actin probe. Quantitation of expression of C4-2 and β actin was done by Imagequan of the Molecular Dynamics Phosphor Imager.

6.1.6 QUANTITATION OF NORTHERN AND SOUTHERN BLOTS

Quantitation of Northern and Southern blots was performed using the ImageQuant™ volume quantitation program from the Molecular Dynamics Phosphor Imager (Sunnyvale, Calif.). Volume quantitation calculates the volume under the surface created by a 3-D plot of pixel locations and pixel values. The volume, (i.e., the integrated intensity of all the pixels in the spot excluding background of the C4-2 bands in Northern and Southern blots was quantitated. These pixel values are then normalized with pixel values in the bands of the housekeeping genes ( D+b 1-+b 2 and β-actin) and are referred to as "relative expression" in the descriptions of the figures in Section 4, above. The subjective terms of "low", "medium" and "high" relative expression are based on C4-2 expression in normal brain as high and in tumor brain tissue as low.

6.2 RESULTS

The modified technique of DD-PCR was used to isolate genes that are differentially expressed either in NBT or GMT. One 3' primer (SEQ ID NO:) and three 5' primers (SEQ ID NOS:) were used to perform the technique of DD-PCR on GMT and NBT as described in Section 6.1.2. Nineteen bands were isolated that showed differential expression either in GMT or NBT. Fourteen of these bands were expressed at higher levels in GMT and four in NBT. See FIG. 1A.

All of these bands were isolated, DNA was eluted, reamplified and cloned into the PCRII vector from Invitrogen (San Diego, Calif.). Sequence analysis of these clones has indicated that the majority of these genes have no homology to known sequences in the National Database (NCBI, Bethesda, Md.). One particular clone, clone C4-2, appears to be unique because it shows higher expression in NBT than GMT (see FIGS. 1A and 1B).

Using the gene specific RT-PCR technique as described in Section 6.1.3, C+b 4-+b 2 was found to be expressed 50 fold higher in NBT and as compared to GMT (FIG. 2). As demonstrated in FIG. 2A and 2D, C+b 4-+b 2 was not detected in a B cell lymphoma or meningioma tumor sample. Also as demonstrated in FIG. 2, more particularly in FIG. 2B, expression of a tumor associated gene (D2-2) was higher in GMT than in NBT. D2-2 thus served as a negative control. D1-2, a gene expressed consistently in normal and tumor samples and was used as an internal control (see FIG. 2C). The results presented in FIG. 2 clearly demonstrate that C4-2 is differentially expressed in NBT and not in GMT.

6.2.1 SEQUENCE ANALYSIS OF CLONE C4-2

Clone C4-2 that was isolated by DD-PCR was only 250 base pairs in length and has a long polyA tail. This clearly indicates that C4-2 sequence is at 3' end of the gene. Sequence homology analysis of the 250 bp fragment of C+b 4-+b 2 indicates that it has 66.8% homology to ARPP-16 (see FIG. 3). Northern blot analysis of RNA isolated from Brain tissue using the 250 bp sequence shown in FIG. 3 shows that there are two natural transcripts of C+b 4-+b 2, which are 1.6 and 6.0 Kb. (data not shown).

ARPP-16 is a phosphoprotein which is expressed in cells with increased cAMP levels. ARPP-16 has homology to another protein of a different molecular weight and is referred to as ARPP-19. ARPP-16 and 19 involve a combination of alternative promoters and splicing rather than the conventional differential splicing of an identical primary transcript. Both of these proteins are shown to be expressed in brain and are enriched in the basal ganglia (Brene et al., 1994, J. Neuroscience 14:985–998; Horiuchi et al., J. Biol Chem. 265:9476–9484). The exact function of these proteins is not known but they are thought to mediate the action of neurotransmitters of hormones that raise cAMP levels in cells. (Brene et al., supra; Horiuchi et al., supra).

Using the 250 bp C4-2 fragment as a probe, a human brain library was screened and a clone with a 2.0 Kb insert was isolated. Sequence analysis showed that this clone corresponds to the 6.0 Kb natural transcript.

6.2.2 EXPRESSION OF C4-2 IN BRAIN TUMOR CELL LINES AND NORMAL HUMAN ASTROCYTES (FETAL)

C4-2 is expressed at high levels in NBT but very low expression in GMT (see FIG. 2). The expression of C4-2 in cell lines derived from different human brain tumors and normal human astrocytes (fetal) was determined as described in Section 6.1.3. As shown in FIG. 4, C4-2 is expressed at very low levels in Glioblastoma, gradeIV Astrocytomas, Glioma, Neuroectodermal, Medulloblastoma and Fetal Normal Human Astrocytes (FNHA). These cell lines showed a high level of D2-2 expression (a novel tumor associated gene). Connexin 43, a tumor suppressor gene (see Cheu et al., 1995, Cell Growth Differ 6:681–690) shows similar expression levels in some brain tumor cell lines (data not shown). This experiment clearly demonstrates that C4-2 is expressed at very low levels in a majority of the brain tumor cell lines. Thus C4-2 appears to serve as a potential tumor suppressor gene.

6.2.3 EXPRESSION OF C4-2 IN TUMOR TISSUES

Since C4-2 is overexpressed in NBT as compared to GMT, its expression in other tumor tissues was determined as described above. As shown in FIG. 5, C4-2 is expressed at very low levels in Glioblastoma, meningiomas, colon cancer metastatic to brain, recurrent glioma, diffuse malignant brain lymphoma of the B cell type, breast ductal carcinoma, prostate adenocarcinoma with a Gleason score of 9 and prostate tumor cell line (LNCAP). D2-2, as a control does show high expression in these tumor samples. This experiment confirms the fact that low expression of C4-2 is not only confined to brain tumor tissues but also to other tumor types.

6.2.4 EXPRESSION OF C4-2 IN DIFFERENT REGIONS OF NORMAL HUMAN BRAIN

To understand the function of C4-2 in brain, it is important to investigate its expression in different regions of the brain. Eight different regions of the normal human brain were studied for this purpose. As shown in FIG. 6, C4-2 is expressed at high levels in cerebellum, occipital lobe, temporal lobe, frontal lobe, putamen and cerebral cortex. Low levels of C4-2 were observed in medulla and spinal cord. The reason for such a selective distribution of expression is not known at present. It would be of interest to study the cellular distribution of C4-2 expression in these regions by in situ hybridization.

6.2.5 EXPRESSION OF C4-2 IN NORMAL HUMAN TISSUE

To study the expression of C4-2 in different tissues, Northern blot analysis using C4-2 as a probe as performed as described in Section 6.1.5. As shown in FIG. 7, C4-2 is expressed at very high levels in brain, moderate level in placenta, liver, kidney, pancreas and at low levels in a number of tissues such as heart, lung, skeletal muscle, spleen, thymus, prostate, testis, ovary, small intestine, colon (Mucosal lining) and peripheral blood leucocytes. High C4-2 expression in brain confirms that it has specific function in brain; however, the reason for selective distribution in placenta, liver, kidney and pancreas is not known at present.

6.3 DISCUSSION

C4-2 is overexpressed in normal brain tissue and is essentially not detected in glioblastoma multiforme and cell lines derived from other types of brain tumors. C4-2 has high expression in brain tissue and is widely expressed in different regions of tissue isolated from the human brain. C4-2 was detected at very low levels, if at all, in a number of adult human brain tumor cell lines, including glioblastoma, astrocytoma III, astrocytomal V, glioma, medulla blastoma, neuroectodermal and neuroblastoma. In addition, C4-2 is expressed at minimal levels in normal fetal astrocytes.

The present invention has utility in elucidating the process of tumorigenesis for early detection of brain tumors, including but not limited to highly malignant brain tumors, and provides better strategies for effective treatment of brain tumors.

7. DEPOSIT OF MICROORGANISM

Bacteria strain *E. coli* designated NWB-C4-2 containing plasmid C4-2, containing an 250 base pair EcoRI fragment was deposited on Nov. 5, 1996 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 98,247.

The present invention is not to be limited in scope by the microorganism deposited or the specific embodiments described herein. The above examples are presented for purposes of illestration only and are not intended to limit the scope of the invention in any way. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

---

What is claimed is:

1. An isolated nucleic acid hybridizable under high stringency conditions to a C4-2 DNA sequence consisting of the nucleotide sequence of FIG. 3, SEQ ID NO.:2.

2. An isolated nucleic acid comprising a nucleotide sequence of FIG. 3, SEQ ID NO.: 2 that is detected at higher levels in normal brain tissue than in glioblastoma brain tumor tissue.

3. A nucleotide vector containing the nucleotide sequence of claim 1 or 2.

4. An expression vector containing the nucleotide sequence of claim 1 or 2 in operative association with a nucleotide regulatory sequence that controls expression of the nucleotide sequence in a host cell.

5. An isolated genetically engineered host cell that contains the nucleotide sequence of claim 1 or 2.

\* \* \* \* \*